United States Patent
Eyer et al.

(10) Patent No.: US 11,096,986 B2
(45) Date of Patent: Aug. 24, 2021

(54) USE OF A NEUROFILAMENT PEPTIDE FOR TARGETING NEURAL STEM CELLS

(71) Applicants: Universite D'Angers, Angers (FR); Institut National de la Sante et de la Recherche Medicale (INSERM), Paris (FR)

(72) Inventors: Joel Eyer, Blaison-Gohier (FR); Claire Lepinoux-Chambaud, Confolens (FR)

(73) Assignees: Universite D'Angers, Angers (FR); Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 15/321,338

(22) PCT Filed: Jun. 23, 2015

(86) PCT No.: PCT/EP2015/064118
§ 371 (c)(1),
(2) Date: Dec. 22, 2016

(87) PCT Pub. No.: WO2015/197619
PCT Pub. Date: Dec. 30, 2015

(65) Prior Publication Data
US 2017/0157208 A1    Jun. 8, 2017

(30) Foreign Application Priority Data

Jun. 23, 2014  (EP) .................................... 14305981

(51) Int. Cl.
| | | |
|---|---|---|
| *A61K 38/17* | (2006.01) | |
| *A61K 38/16* | (2006.01) | |
| *A61K 47/64* | (2017.01) | |
| *A61K 45/06* | (2006.01) | |
| *G01N 33/574* | (2006.01) | |
| *G01N 33/569* | (2006.01) | |

(52) U.S. Cl.
CPC .............. *A61K 38/17* (2013.01); *A61K 38/16* (2013.01); *A61K 45/06* (2013.01); *A61K 47/64* (2017.08); *G01N 33/56966* (2013.01); *G01N 33/57407* (2013.01)

(58) Field of Classification Search
CPC ........ A61K 38/17; A61K 38/16; A61K 47/64; A61K 45/06; G01N 33/57407; G01N 33/56966; A61P 43/00; A61P 35/00; A61P 25/28; A61P 25/00
See application file for complete search history.

(56) References Cited

U.S. PATENT DOCUMENTS

| | | | |
|---|---|---|---|
| 2006/0270834 A1 | 11/2006 | Kanno | |
| 2013/0004429 A1* | 1/2013 | Eyer | ...................... A61K 38/16 424/9.6 |
| 2013/0012452 A1* | 1/2013 | Basile | .................. A61K 48/005 514/19.8 |

FOREIGN PATENT DOCUMENTS

| | | | | |
|---|---|---|---|---|
| WO | 2009/136007 A1 | 11/2009 | | |
| WO | WO-2011073207 A1 * | 6/2011 | ............. | A61K 38/16 |

OTHER PUBLICATIONS

Meijer et al. Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.*
Lane, A.L. et al., "Brain tumour targeting strategies via coated ferrociphenol lipid nanocapsules", European Journal of Pharmaceutics and Biopharmaceutics, 2012, vol. 81, No. 3, pp. 690-693.
Balzeau, J. et al., "The effect of functionalizing lipid nanocapsules with NFL-TBS.40-63 peptide on their uptake by glioblastoma cells", Biomaterials, 2013, vol. 34, No. 13, pp. 3381-3389.
Lepinoux-Chambaud, C. et al., "The NFL-TBS.40-63 anti-glioblastoma peptide esters selectively in glioma cells by endocytosis", International Journal of Pharmaceutics, 2013, vol. 454, No. 2, pp. 738-747.
Agasse et al., 2004. Neurogenic and intact or apoptotic non-neurogenic areas of adult brain release diffusible molecules that differentially modulate the development of subventricular zone cell cultures. Eur J. Neurosci. Mar. 2004;19(6):1459-68.
Ahmed et al., 2009. Transcription factors and neural stem cell self-renewal, growth and differentiation. Cell Adh Migr. 3(4):412-24.
Azari et al. (2010) Isolation and expansion of the adult mouse neural stem cells using the neurosphere assay. J Vis Exp (45), pp. 1-4.
Beckervordersandforth et al. (2010) In vivo fate mapping and expression analysis reveals molecular hallmarks of prospectively isolated adult neural stem cells. Cell Stem Cell 7 (6):744-758.
Berges et al. (2012) A tubulin binding peptide targets glioma cells disrupting their microtubules, blocking migration, and inducing apoptosis. Mol Ther 20 (7)1367-1377.
Bexell et al. (2013) Stem cell-based therapy for malignant glioma. Cancer Treat Rev 39 (4):358-365.
Bocquet et al. (2009) Neurofilaments bind tubulin and modulate its polymerization. J Neurosci 29 (35):11043-11054.
Coskun V, Wu H, Bianchi B, Tsao S, Kim K, Zhao J, Biancotti JC, Hutnick L, Krueger RC, Jr., Fan G, de Vellis J, Sun YE (2008) CD133+ neural stem cells in the ependyma of mammalian postnatal forebrain. Proc Natl Acad Sci U S A 105 (3):1026-1031.
Gage, Fred H. (2000) Mammalian neural stem cells. Science 287 (5457):1433-1438.

(Continued)

*Primary Examiner* — Gregory S Emch
(74) *Attorney, Agent, or Firm* — Banner & Witcoff, Ltd.

(57) ABSTRACT

The present invention shows that the isolated NFL-TBS$_{40-63}$ peptide is highly specific for neural stem cells. It is therefore presented here for use in a method for detecting these cells in vitro or in vivo, for addressing chemical compounds or biological materials to said cells, or for treating neurodegenerative disorders or brain tumours.

13 Claims, 9 Drawing Sheets

Specification includes a Sequence Listing.

(56) References Cited

OTHER PUBLICATIONS

Hall et al. (1989) Stem cells: the generation and maintenance of cellular diversity. Development 106 (4):619-633.
Jo et al. (2012) Regulation of differentiation potential of human mesenchymal stem cells by intracytoplasmic delivery of coactivator-associated arginine methyltransferase 1 protein using cell-penetrating peptide. Stem Cells 30 (8):1703-1713.
Johnson et al. (2005) Direct evidence that neural cell adhesion molecule (NCAM) polysialylation increases intermembrane repulsion and abrogates adhesion. J Biol Chem 280 (1):137-14.
Katsetos et al. (2009) Tubulin targets in the pathobiology and therapy of glioblastoma multiforme. I. Class III beta-tubulin. J Cell Physiol 221 (3):505-513.
Kim et al. (2013) Neural stem cell-based treatment for neurodegenerative diseases. Neuropathology 33 (5):491-504.
Lei et al. (2008) Applications of mesenchymal stem cells labeled with Tat peptide conjugated quantum dots to cell tracking in mouse body. Bioconjug Chem 19 (2):421-427.
Lendahl et al. (1990) CNS stem cells express a new class of intermediate filament protein. Cell 60 (4):585-595.
Nakamura et al. (2003) Expression of tubulin beta II in neural stem/progenitor cells and radial fibers during human fetal brain development. Lab Invest 83 (4):479-489.
Oh et al. 2009. Novel treatment strategies for malignant gliomas using neural stem cells. Neurotherapeutics. 6 (3):458-64. doi: 10.1016/j.nurt.2009.05.003.
Reigner et al. Estimating the starting dose for entry into humans: principles and practice. European Journal of Clinical Pharmacology. 2002;57(12):835-845.
Reynolds et al. (1992) Generation of neurons and astrocytes from isolated cells of the adult mammalian central nervous system. Science 255 (5052):1707-1710.
Shah et al. (2007) Labeling of mesenchymal stem cells by bioconjugated quantum dots. Nano Lett 7 (10):3071-3079.
Stewart et al. (2008) Cell-penetrating peptides as delivery vehicles for biology and medicine. Org Biomol Chem 6 (13):2242-2255.
Suh et al. (2007) In vivo fate analysis reveals the multipotent and self-renewal capacities of Sox2+ neural stem cells in the adult hippocampus. Cell Stem Cell 1 (5):515-528.
Taupin Philippe. 201t Neurogenic drugs and compounds to treat CNS diseases and disorders. Cent Nery Syst Agents Med Chem. 1;11(1):35-7.
Weigmann et al. (1997) Prominin, a novel microvillispecific polytopic membrane protein of the apical surface of epithelial cells, is targeted to plasmalemmal protrusions of non-epithelial cells. Proc Natl Acad Sci U S A 94 (23):12425-12430.
Yukawa et al. (2010) Transduction of cell-penetrating peptides into induced pluripotent stem cells. Cell Transplant 19 (6):901-909.
Grabb et al. "Dissemination of Supratentorial Malignant Gliomas via the Cerebrospinal Fluid in Children Experimental and Clinical Study" Neurosurgery 1992-98, Jan. 1992, vol. 30: 64-71, No. 1.
Junes-Gill et al. "hHSS1: a novel secreted factor and suppressor of glioma growth located at chromosome 19q13.33". J. Neurooncol. (2011) 102:197-211.
Mistry et al. "Cancer Dissemination, Hydrocephalus, and Survival After Cerebral Ventricular Entry During High-Grade Glioma Surgery: A Meta-Analysis" Neurosurgery, vol. 83, No. 6, Dec. 2018.
Waga et al. "Intratumoral Hemorrhage after a Ventriculoperitoneal Shunting Procedure". Neurosurgery, vol. 9. No. 3, 1981.
Liu et al. "Transcriptional signaling pathways inversely regulated in Alzheimer's disease and glioblastoma multiform". Scientific Reports, 3:3467, 2013.

* cited by examiner

USE OF A NEUROFILAMENT PEPTIDE FOR TARGETING NEURAL STEM CELLS

BACKGROUND OF THE INVENTION

Neural stem cells (NSCs or NSC) are located in two major neurogenic regions in the adult brain: the sub-ventricular zone (SVZ) and the dentate gyrus of the hippocampus (Gage 2000). They are characterized by their capacity to self-renew, to form neurospheres in culture, to proliferate, and to generate neurons, astrocytes and oligodendrocytes (multipotency) (Hall et Wat, 1989; Reynolds et Weiss, 1992; Azari et al., 2010). The characteristics of these cells provide new therapeutic approaches. The use of normal or genetically modified NSC has already been described for the treatment of neurodegenerative disorders (Parkinson, Huntington and Alzheimer's diseases, Amyotrophic Lateral Sclerosis) and for the treatment of malignant glioma. The development of neural stem cell-based therapies may be beneficial to target these cells, increase their mobilization and stimulate neurogenesis for regenerative medicine and for the treatment of brain tumours (see Kim et al., 2013, and Bexell et al., 2013 for review).

NSCs moreover have a great potential for drug screening. Yet, it is still difficult to identify these cells and to target therapeutic molecules in them.

Since the discovery of adult neural stem cells, the extent to which stem cells have common hallmarks, either in the same tissue from development into adulthood or across different adult tissues, has been a key issue. The transcription factor SOX2, the intermediate filament proteins Nestin and Vimentin, and the membrane protein Prominin1 have been suggested as common molecular markers for NSCs across different regions and ontogenies (Lendahl et al., 1990, Suh et al., 2007, Weigmann et al., 1997). However, these markers are rather widespread in the adult brain, with SOX2 being expressed in all astrocytes (Suh et al., 2007) and Nestin and Prominin1 present in all ependymal cells lining the ventricle Beckervordersandforth et al., 2010, Coskun et al., 2008).

Moreover, conventional methods for the isolation and characterization of NSC depend on their behavior in a defined culture medium such as neurosphere formation and immunodetection of marker molecules. These methods, however, are time-consuming and involve the use of a number of antibodies, which may render the cells unsuitable for further experimental and therapeutic applications.

Therefore, a need exists to develop novel chemical compounds that are useful for the detection of neural stem cells.

Moreover, there is also a need to identify compounds that would target these cells specifically, in order to deliver therapeutic drugs inside them (thereby increasing their mobilization and/or stimulating neurogenesis, for example).

In this context, the inventors have shown for the first time that the microtubule-depolymerizing peptide called "NFL-TBS$_{40-63}$" has a unique specificity in vitro and in vivo for neural stem cells.

The results presented below reveal that the NFL-TBS$_{40-63}$ peptide can translocate massively in neural stem cells of new-born and adult rats through a dose-dependent uptake. Moreover, when injected in the lateral ventricle of adult rat, the NFL-TBS$_{40-63}$ peptide is located in the ependymal layer and a part of it in the sub-ependymal area, showing that the peptide can also enter in vivo in the SVZ to target neural stem cells. Altogether, these results demonstrate a selective uptake of this peptide by neural stem cells both in cell cultures and in animal models.

The present inventors also demonstrated that the NFL-TBS$_{40-63}$ peptide has no major cytotoxic effect on NSCs, when used at low concentration (typically below 40 μmol/L). It may therefore be safely used in order to target therapeutical drugs to NSCs in humans.

The present inventors also showed that, at higher concentrations (typically above 40 μmol/L), the NFL-TBS$_{40-63}$ peptide reduces the self-renewal capacity of NSCs in vitro, by enhancing their differentiation state and their adhesion (cf. FIGS. 4 and 5). It may therefore be used in patients suffering from neurodegenerative diseases (e.g., by replacing dying cells) or in patients suffering from brain cancers (e.g., by reducing the proliferation of stem cells that are often responsible of tumour recurrence).

The present inventors therefore propose to use the NFL-TBS$_{40-63}$ peptide:
  i) to label NSC in order to follow them, or to modulate their properties (their self-renewal or their differentiation), as previously shown with the Tat and RGD peptides coupled with fluorescent quantum dots for mesenchymal stem cells (Shah et al., 2007; Lei et al., 2008; Jo et al., 2012); or
  ii) as a delivery system using functionalized nanoparticles, as previously demonstrated in glioblastoma cells (Balzeau et al., 2013).

DESCRIPTION OF THE INVENTION

The present inventors have shown for the first time that the microtubule-depolymerizing peptide called "NFL-TBS$_{40-63}$" has a unique specificity in vitro and in vivo for neural stem cells and may be used for delivering therapeutical compounds into these particular cells.

The NFL-TBS$_{40-63}$ peptide corresponds to the sequence of the tubulin-binding site located along the neurofilament light subunit. This peptide has been previously shown by the present inventors to target glioblastoma cells in vitro and in vivo, for which it is able to disrupt the microtubule network (Bocquet et al., 2009; Bergès et al., 2012; Balzeau et al., 2013; Lépinoux-Chambaud et Eyer, 2013). In the meantime, these studies highlighted a very low level of internalization for slow proliferative healthy cells from the nervous system, including astrocytes, oligodendrocytes or neurons (Bocquet et al., 2009). It is therefore surprising that the same peptide is able to specifically target and penetrate into healthy cells, let alone neural stem cells.

In fact, the inventors herein demonstrate that the cellular mechanisms involved in NFL-TBS$_{40-63}$ uptake by NSCs fundamentally differ from the ones previously observed in other cells.

First, the uptake mechanism of NFL-TBS$_{40-63}$ in NSC fundamentally differs from the one observed in glioblastoma cells. In glioblastoma cells the peptide is only internalized by endocytosis (Lépinoux-Chambaud et Eyer, 2013), while in neural stem cells it can translocate directly through the membrane by a passive transport, which is temperature and energy-independent. This was also confirmed using a complete panel of inhibitors of endocytosis. This result indicates that the NFL-TBS$_{40-63}$ peptide uses in NSC a unique entry pathway that is different from other cell-penetrating peptides, like R8 and Tat, which transduce in induced pluripotent stem cells (iPS cells) through macropinocytosis, an endocytic pathway (Yukawa et al., 2010).

Second, the specific effect of the NFL-TBS$_{40-63}$ peptide on glioblastoma cells to disrupt the microtubule network and to block the cell cycle is not observed on neural stem cells. Tubulin immunostaining in neural stem cells revealed a well-organized microtubule network after peptide incubation. Longer treatment with the peptide did not affect the cell cycle and the viability of neural stem cells. One possibility could be the high level expression of βIII-tubulin in glioblastoma, while the neural stem cells and progenitors expressed the βII-tubulin (Namakura et al., 2003; Katsetos et al., 2009).

Third, high concentration of the NFL-TBS$_{40-63}$ peptide disrupts the self-renewal capacity of neural stem cells, decreasing the number of secondary neurospheres compared with untreated cells. This effect could be explained by an increased attachment of the neurospheres in the presence of the peptide, and a possible increase of differentiated cells. This effect is specific of neural stem cells.

DEFINITIONS

Neural stem cells are self-renewing, multipotent cells that generate the main phenotypes of the nervous system. Stem cells are characterized by their capability to differentiate into multiple cell types via exogenous stimuli from their environment. They undergo asymmetric cell division into two daughter cells, one non-specialized and one specialized. NSCs primarily differentiate into neurons, astrocytes, and oligodendrocytes (Hall et Wat, 1989; Reynolds et Weiss, 1992; Azari et al., 2010).

The NFL-TBS$_{40-63}$ peptide is a 24 amino acids long polypeptide having the following sequence: YSSYSAPVSSSLSVRRSYSSSSGS (SEQ ID NO:1). In the context of the present application, it is referred to as the "peptide used in the invention". As mentioned previously, it corresponds to the second tubulin-binding site of the light neurofilament subunit (amino acids 40 to 63 of the TBS site of the NFL protein).

This peptide was previously disclosed to affect the proliferation of glioma cells. Yet, at that time, it was disclosed has having poor, if not undetectable, effects on normal astrocytes or neurons (Bocquet et al., 2009). Its effect on neural stem cells has never been assessed nor suggested so far.

The "isolated amino acid sequence" used in the methods of the invention comprises the NFL-TBS$_{40-63}$ peptide but cannot be the entire neurofilament light subunit itself, because this protein has not the same biological activity as its fragment (i.e. the NFL-TBS$_{40-63}$ peptide). In particular, the entire NFL protein is not able to penetrate into NSCs. Thus, the isolated amino acid sequence of the invention comprises the NFL-TBS$_{40-63}$ peptide provided but not the entire neurofilament light (NFL) subunit itself.

In general, the isolated amino acid sequence used in the methods of the invention comprises no more than 100 amino acids, preferably no more than 50 amino acids.

In a preferred embodiment, the isolated amino acid sequence used in the methods of the invention consists of the NFL-TBS$_{40-63}$ peptide (of SEQ ID NO: 1) or a biologically active derivative thereof. Preferably, it consists of the NFL-TBS$_{40-63}$ peptide (of SEQ ID NO: 1) itself.

The methods of the invention may moreover use "biologically active derivatives of the NFL-TBS$_{40-63}$ peptide". As used herein, the term "peptide derivative" includes the variants and the fragments of the peptide to which it refers. Therefore, the "derivatives" of the second tubulin-binding site of the light neurofilament subunit (namely NFL-TBS$_{40-63}$ (SEQ ID NO: 1)) include variants and fragments of the NFL-TBS$_{40-63}$ peptide. More particularly, in the context of the invention, the derivative designates "biologically active" variants and fragments of this peptide, i.e., variants and fragments retaining the biological activity and the specificity of the parent NFL-TBS$_{40-63}$ peptide. Thus, in the context of the invention, the "biologically active" derivatives of the NFL-TBS$_{40-63}$ peptide have to show a high specificity toward neural stem cells, as the parent NFL-TBS$_{40-63}$ peptide. Said derivatives of the NFL-TBS$_{40-63}$ peptide have preferably the same specificity as the parent NFL-TBS$_{40-63}$ peptide toward NSCs, as assessed in vitro by conventional cellular uptake experiments. Cellular uptake of the peptide may be measured by contacting said peptide with cells in which endocytosis has been inhibited (for example, by maintaining said cells at 4° C. or by depleting the cells of ATP), and by measuring the amount of the peptide, which is found inside the cells (e.g., by immunochemistry).

In a preferred embodiment, the derivative of the NFL-TBS$_{40-63}$ peptide is a biologically active fragment of the NFL-TBS$_{40-63}$ peptide. Said fragment comprises at least 12 successive amino acids of the parent NFL-TBS$_{40-63}$ peptide, preferably at least 16, more preferably at least 18 amino acids, and is characterized in that it retains the specificity of the parent NFL-TBS$_{40-63}$ peptide.

In another preferred embodiment, the derivative of the NFL-TBS$_{40-63}$ peptide is a biologically active variant of the NFL-TBS$_{40-63}$ peptide. Said variant can be either an allelic variant of the peptide, or a peptidomimetic variant of the peptide. An "allelic variant of the peptide" has the same amino acid sequence as the NFL-TBS$_{40-63}$ peptide, except that one or more amino acids have been replaced by other amino acids or suppressed, the final peptide retaining the specificity of the parent NFL-TBS$_{40-63}$ peptide. Preferably, such allelic variant has 70%, preferably 80%, more preferably 90% and even more preferably 95% of identity as compared with the parent NFL-TBS$_{40-63}$ peptide (of SEQ ID NO:1). For example, such allelic variant can be the TBS motif of the neurofilament light subunit of the quail, which retains 20 over 24 amino acids of the NFL-TBS$_{40-63}$ peptide. The variant of the peptide can also be a peptidomimetic variant, which is an organic molecule that mimics some properties of the parent peptide, including its specificity toward NSCs. Preferred peptidomimetics are obtained by structural modification of peptides according to the invention, preferably using unnatural amino acids, D amino acid instead of L amino acids, conformational restraints, isosteric replacement, cyclization, or other modifications. Other preferred modifications include, without limitation, those in which one or more amide bond is replaced by a non-amide bond, and/or one or more amino acid side chain is replaced by a different chemical moiety, or one of more of the N-terminus, the C-terminus or one or more side chain is protected by a protecting group, and/or double bonds and/or cyclization and/or stereospecificity is introduced into the amino chain to increase rigidity and/or binding affinity. Still other preferred modifications include those intended to enhance resistance to enzymatic degradation, improvement in the bioavailability, and more generally in the pharmacokinetic properties, compared to the parent NFL-TBS$_{40-63}$ peptide. It is noteworthy that changing the C-terminal part for an amide (thereby protecting same from a fast proteolytic degradation) does not affect the targeting properties of the NFL-TBS$_{40-63}$ peptide.

All of these variations are well known in the art. Thus, given the peptide sequences of the NFL-TBS$_{40-63}$ peptide, those skilled in the art are enabled to design and produce peptidomimetics having biological characteristics similar to or superior to the NFL-TBS$_{40-63}$ peptides. Preferred peptidomimetic variants of the NFL-TBS$_{40-63}$ peptide retain the specificity of the NFL-TBS$_{40-63}$ peptide toward NSCs.

The peptides used in the invention (namely the amino acid sequence comprising the NFL-TBS$_{40-63}$ peptide or its fragments, its peptidomimetic or allelic variants) can be conveniently synthesized using art recognized techniques.

As used herein, "percentage of identity" between two amino acid sequences denotes the percentage of amino acids residues that are identical between the two sequences to be compared, obtained after the best alignment (optimum alignment), this percentage being purely statistical and the differences between the two sequences being distributed randomly and along their entire length. Sequence comparisons between two amino acid sequences can be performed for example with the BLAST program available on the website http://www.ncbi.nlm.nih.gov/gorf/b12.html, the parameters used being those given by default (in particular for the parameters "open gap penalty":5 and "extension gap penalty":2, the matrix selected being for example the "BLOSUM 62" matrix as suggested by the program, the percentage identity between the two sequences to be compared being calculated directly by the program).

As used herein, the term "biological sample" or "sample" designates a cell culture that is handled in vitro. The cells in culture can be either of lineage origin or of primary origin. In this second case, the cells can be extracted from an animal brain following a biopsy or a surgical operation.

Use of the NFL-TBS$_{40-63}$ peptide to target NSCs

Targeting neural stem cells is promising for the development of new regenerative strategies, because NSCs are present in the adult brain where they are able to proliferate, self-renew and differentiate into new neurons, astrocytes and oligodendrocytes.

The present inventors herein show that the NFL-TBS$_{40-63}$ peptide is able to translocate passively in neural stem cells in vitro, and, when injected in the cerebrospinal fluid of rats, to target adult neural stem cells in vivo without causing cytotoxicity. Moreover, the in vitro formation of neurospheres was not altered by the presence of this peptide, whereas the self-renewal capacity of these cells was slightly reduced and associated with an increase of adherent cells and a decreased of NSC proliferation. These results indicate that the NFL-TBS$_{40-63}$ peptide represents a new molecular tool to target neural stem cells and may be used in new strategies for regenerative medicine and treatment of brain tumours. More particularly, NSCs uptake of the NFL-TBS$_{40-63}$ peptide will increase or induce the differentiation of these cells (thereby replacing dying cells) and will thus benefit to patients suffering from neurodegenerative disorders. Alternatively, by favouring differentiation of cancerous NSCs, the NFL-TBS$_{40-63}$ peptide may decrease their aberrant proliferation and thus benefit to patients suffering from brain cancers.

In a first aspect, the present invention therefore relates to the use of an isolated amino acid sequence comprising the NFL-TBS$_{40-63}$ peptide (SEQ ID NO: 1), or a biologically active derivative thereof, for targeting chemical compounds or biological materials to neural stem cells in vitro.

Alternatively, the present invention relates to an isolated amino acid sequence comprising the NFL-TBS$_{40-63}$ peptide (SEQ ID NO: 1), or a biologically active derivative thereof, for use in a method for targeting chemical compounds or biological materials to neural stem cells in vivo.

Also, the present invention relates to a method for targeting chemical compounds or biological materials to neural stem cells in vivo in a subject in need thereof, or in vitro.

Such chemical compounds or biological material can be directly coupled to the NFL-TBS$_{40-63}$ peptide, or they can be contained in appropriate carriers (e.g., nanocapsules, liposomes, micelles, or any encapsulation mean that is known by the man skilled in the art) that are coupled to the NFL-TBS$_{40-63}$ peptide.

Said chemical compounds or biological material can be pharmaceutical compounds and/or labeling markers. Examples of such compounds/markers are disclosed below.

This targeting method may thus be used to treat patients in need thereof, or to detect neural stem cells in vitro or in vivo.

Use of Conjugated-NFL-TBS$_{40-63}$ Peptide to Treat Diseases Related to NSCs

In a subsequent aspect, the present invention provides pharmaceutical compositions containing the NFL-TBS$_{40-63}$ peptide (SEQ ID NO:1), or a biologically active derivative thereof, for use in a method for treating patients in need thereof.

As disclosed above, the NFL-TBS$_{40-63}$ peptide (of SEQ ID NO:1), or biologically active derivative thereof may be used alone in order to favor NSCs differentiation or reduce NSCs self-renewal in vivo.

In this case, the present invention relates to the use of an isolated amino acid sequence comprising the NFL-TBS$_{40-63}$ peptide (SEQ ID NO: 1) or a biologically active derivative thereof for the manufacture of a pharmaceutical composition for treating patients in need thereof.

The concentration of the NFL-TBS$_{40-63}$ peptide in this pharmaceutical composition should be high enough so as to induce a pharmaceutical effect (on differentiation or self-renewal) on its own. This high concentration is typically of at least about 0.04 mg/kg, the maximum recommended starting dose MRSD being of about 4 μg/kg. These values are based on the amount of the peptide injected in the rats (57 μg for a weight of about 230 g) and on the $K_m$ values usually used for the rat (=6) and for a human (=37) (Reigner B. et al, 2002).

Alternatively, the NFL-TBS$_{40-63}$ peptide (of SEQ ID NO:1) or biologically active derivative thereof may be covalently linked (or conjugated) to another compound.

In this latter case, the present invention relates to the use of an isolated amino acid sequence comprising the NFL-TBS$_{40-63}$ peptide (SEQ ID NO: 1) or a biologically active derivative thereof for the manufacture of a pharmaceutical conjugates for treating patients in need thereof.

As used herein, the term "pharmaceutical conjugates" designates any conjugated molecule containing the NFL-TBS$_{40-63}$ (SEQ ID NO: 1) or a biologically active derivative thereof. This conjugated molecule can be:
  a fusion protein containing the NFL-TBS$_{40-63}$ (SEQ ID NO: 1) or a biologically active derivative thereof,
  a chemical compound or a biological material that is directly coupled to the NFL-TBS$_{40-63}$ peptide or a biologically active derivative thereof, or
  a chemical compound or a biological material which is contained in an appropriate carrier (e.g., nanocapsules, liposomes, micelles), said carrier being coupled to the NFL-TBS$_{40-63}$ peptide or a biologically active derivative thereof.

The said chemical compound or a biological material can be of any nature.

In a preferred embodiment, said chemical compound or biological material is intended to treat neurodegenerative disorders. It is then preferably chosen in the group consisting of: differentiation factors (such as AMPA, piracetam, SCS-111, FK-960, apigenin and the like), and transcription factors affecting self-renewal (such as SOX2 or CBF1), proliferation (such as OLIG2 or ID2) or differentiation (such as MASH1 or PAX6). These factors are reviewed in Ahmed et al, 2009 and in Taupin et al, 2011

In a preferred embodiment, said chemical compound or biological material is intended to treat brain cancers. It is then preferably a molecule that activates or inhibits surface receptors, or a cytokine (HGH, SCF, VEGF and the like). These molecules are disclosed in Oh and Lim, 2009.

The NFL-TBS$_{40-63}$ peptide may for example address transcription factors (such as SOX2, CBF1, OLIG2, ID2, MASH1, PAX6 or those mentioned in Ahmed et al, 2009) specifically to the neural stem cells, thereby increasing their mobilization, stimulating neurogenesis and/or modulating their differentiation, their migration, their proliferation, and/or their self-renewal.

Of note, when the NFL-TBS$_{40-63}$ peptide is used as a carrier to target other compounds to NSCs (e.g., encapsulated compounds), its concentration will be too low to induce a pharmaceutical effect (on differentiation or self-renewal) on its own.

In another embodiment, the present invention relates to a method of therapeutically treating patients in need thereof, by administering them an effective amount of a pharmaceutical composition containing said pharmaceutical composition or said pharmaceutical conjugates. Patients that may benefit from this therapeutical use and method are for example patients suffering from brain tumours or neurodegenerative diseases.

Brain tumours, and, more particularly glioblastoma, involve the aberrant development of NSCs into tumour stem cells. These cells are usually resistant to conventional treatments and favour the recidive of the tumour.

Neurodegenerative diseases are not directly linked to NSCs, since these cells are not responsible of neurodegeneracy. However, NSCs represent, in the human brain, a natural source of new cells that contribute to the repair and replacement of degenerated neurons. These neurodegenerative diseases are for example: the Alzheimer's disease, corticobasal degeneration, Creutzfeldt-Jacob disease, fronto-temporal lobar degeneration, Huntington's disease, multiple sclerosis, normal pressure hydrocephalus, organic chronic brain syndrome, Charcot-Marie-Tooth syndrome, Alexander disease, Parkinson's disease, Pick disease, progressive supranuclear palsy, or senile dementia (Alzheimer type).

In a particular embodiment, when the tumor or the neuronal degeneracy is located in the vicinity of a neurogenic zone, the NFL-TBS$_{40-63}$ (SEQ ID NO: 1) or the biologically active derivative thereof may be administered alone in order to enhance the differentiation of neural stem cells.

In the contrary case, i.e., when the tumour or the neuronal degeneracy is located far from any neurogenic zone, the NFL-TBS$_{40-63}$ (SEQ ID NO: 1) or the biologically active derivative thereof may be coupled to pharmacological molecules that favour neurogenesis or the migration of NSCs to a damaged zone. These molecules are for example growth factors or cytokines (such as BDNF, VEGF, CNTF, bGFG, LIF and the like), as disclosed in Agasse et al, 2004.

In a preferred embodiment, said subject is a mammal, preferably a mouse, a rat, a cat, or a dog, and more preferably a human being.

Such a pharmaceutical composition comprises the pharmaceutical conjugates as defined above, as well as a pharmaceutically acceptable carrier.

For the purpose of the invention, suitable pharmaceutically acceptable carriers include, but are not limited to: water, salt solutions (e.g., NaCl), alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxymethylcellulose, and polyvinyl pyrolidone. The pharmaceutical preparations can be sterilized and if desired, mixed with auxiliary agents, e. g., lubricants, preservatives, stabilizers, wetting agents, emulsifiers, salts for influencing osmotic pressure, buffers, coloring, flavoring and/or aromatic substances and the like which do not deleteriously react with the active compounds. The composition, if desired, can also contain minor amounts of wetting or emulsifying agents, or pH buffering agents. The composition can be a liquid solution, a suspension, or an emulsion. Some appropriate precise formulations are described, for example, in Remington, The Science and Practice of Pharmacy, 19th edition, 1995, Mack Publishing Company.

It is possible to administer the peptide of the invention by means of an intravenous injection when the patient is suffering from a glioblastoma (in this case, the blood-brain barrier is altered and become porous to numerous molecules). In this case, the pharmaceutical composition can be formulated in accordance with the routine procedures as a composition adapted for intravenous administration to an individual. Typically, compositions for intravenous administration are solutions in sterile isotonic aqueous buffer.

Yet, in a preferred embodiment the pharmaceutical composition of the invention is a liquid composition that is dedicated to be administered by intracerebral injection. Said intracerebral injection can be obtained for example by using stereotactic neurosurgery, which is now commonly used by surgeons.

The effective dose of a compound according to the invention varies in function of numerous parameters such as, for example, the chosen administration method, the weight, age, sex, and the sensitivity of the individual to be treated. Consequently, the optimal dose must be determined individually, in function of the relevant parameters, by a medical specialist. In order to predict the expected active doses in human from the first animal studies presented hereunder, one can also use the $k_2$ and $C_T$ values as described by Rocchetti et al (2007).

It is foreseen that the effective doses for treating animals (for example rats) range between about 0.01 micromole and 0.1 milimole using a single stereotaxic injection (60 µl), preferably between about 0.02 and 0.08 micromoles. The human brain being in average 700 fold heavier than the rat brain, it is foreseen that the effective doses for treating humans will range between about 0.01 mg/kg and 0.1 mg/kg, preferably between about 0.01 mg/kg and 0.05 mg/kg. These indicated doses are obviously to be adjusted in the context of clinical therapeutic studies.

Use of the NFL-TBS$_{40-63}$ Peptide to Detect NSCs

In another aspect, the present invention relates to the use of the NFL-TBS$_{40-63}$ peptide (SEQ ID NO: 1), or a biologically active derivative thereof, for detecting neural stem cells either in vivo, or in vitro.

In a particular embodiment, the invention relates to a method for testing in vitro a biological sample for the presence or absence of neural stem cells, said method comprising:
 a. Suspending the cells of the sample in an appropriate medium,
 b. Mixing the NFL-TBS$_{40-63}$ peptide or a biologically active derivative thereof with the suspended cells of the sample,
 c. Determining the percentage of cells containing said NFL-TBS$_{40-63}$ peptide, wherein the percentage of cells containing said NFL-TBS$_{40-63}$ peptide corresponds to the percentage of neural stem cells in the sample.

The characteristics of the NFL-TBS$_{40-63}$ peptide and of the biologically active derivative have been previously described.

In a preferred embodiment, this method uses the NFL-TBS$_{40-63}$ peptide (SEQ ID NO: 1) itself.

In a preferred embodiment, said NFL-TBS$_{40-63}$ peptide is labeled so that it is easy to detect the presence or absence of the cells containing the peptide by conventional techniques.

The term "labelled" as used herein refers to any atom or molecule that can be used to provide a detectable (preferably quantifiable) effect, and that can be attached to an amino acid sequence. Labels include but are not limited to dyes, radiolabels such as $^{32}P$, binding moieties such as biotin, haptens such as digoxygenin, luminogenic, phosphorescent or fluorogenic moieties, mass tags; and fluorochromes alone or in combination with quenchers that can suppress or shift emission spectra by fluorescence resonance energy transfer (FRET). Said labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like, preferably by fluorescence. A label may be a charged moiety (positive or negative charge) or alternatively, may be charge neutral. Labels can include or consist of nucleic acid or protein sequence, so long as the sequence comprising the label is detectable.

Preferably, said labels are fluorochromes. Suitable fluorochromes include, for example:
1. fluorescein and derivatives, like hexachloro-fluorescein, tetrachloro-fluorescein, carboxyfluorescein (TAMRA), CAL FLUOR® (CAL Fluor Green 520, CAL FLUOR Gold 540, CAL FLUOR ORANGE 560, CAL FLUOR RED 590, CAL FLUOR RED 635 available from BIOSEARCH TECHNOLOGIES), succinimidyl ester of carboxyfluorescein (succinimidyl ester of 6-carboxy-2',4,4',5',7,7'-hexachlorofluorescein (HEX™) or succinimidyl ester of 6-carboxy-4',5'-dichloro-2',7'dimethoxyfluorescein (JOE™));
2. Rhodamine and derivatives, like 5- or 6-carboxy-X-rhodamine (ROX), N,N,N',N'-tetramethyl-6-carboxy-rhodamine;
3. Cyanine and derivatives like Cy3, Cy3.5, Cy5, Cy5.5;
4. BODIPY® chromophores like 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaz-a-S-indacene-propionic acid, 4,4-difluoro-5,7-diphenyl-4-bora-3a,4a-diaza-s-indacene-3-propionic acid, 4,4-difluoro-5,p-ethoxyphenyl-4-bora-3a,4a-diaza-s-indacene 3-propionic acid and 4,4-difluoro-5-styryl-4-bora-3a,4a-diaza-S-indacene-propionic acid;
5. Texas Red® and derivatives;
6. Pyrenetrisulfonic acid like APTS, HPTS (CASCADE BLUE®); and
7. Eosin and derivatives.

More preferably, said fluorochrome is selected in the group comprising fluorescein and derivatives like hexachloro-fluorescein, tetrachloro-fluorescein, carboxyfluorescein (TAMRA), CAL FLUOR® (CAL Fluor Green 520, CAL FLUOR Gold 540, CAL FLUOR ORANGE 560, CAL FLUOR RED 590, CAL FLUOR RED 635 available from BIOSEARCH TECHNOLOGIES), succinimidyl ester of carboxyfluorescein (succinimidyl ester of 6-carboxy-2',4,4',5',7,7'-hexachlorofluorescein (HEX™) or succinimidyl ester of 6-carboxy-4',5'-dichloro-2',7'dimethoxyfluorescein (JOE™)).

In the context of the invention, preferred conventional techniques to detect such fluorochrome-labeled peptide include, but are not limited to, flow cytometry or fluorescence microscopy.

In this in vitro method, the percentage of cells containing said amino acid sequence "corresponds to" the percentage of neural stem cells in the sample. This means that the percentage of cells containing the NFL-TBS$_{40-63}$ peptide is equivalent to the percentage of neural stem cells in the biological sample at more or less about 5%. When the absolute number of cells in the sample is known, one can also infer from the method of the invention the absolute number of neural stem cells in the sample at more or less about 5%.

The cells are suspended and let grown in vitro in an appropriate medium for stem cells. Such medium is well-known from a person skilled in art and comprises advantageously glucose and L-glutamine, and penicillin/streptomycin. Said medium does not contain fetal calf serum in order to avoid the differentiation of the cells. But the medium advantageously contains EGF and/or FGF and optionally a supplement for neuronal cells (e.g., B27). The cells are conserved in a humidified incubator gassed with 5% $CO_2$ at 37° C.

In step a) of this method, the neurospheres are contacted with the peptide of the invention in the appropriate medium, at 37° C.

Preferably, the concentration of the amino acid sequence to be added is comprised between 1 and 100 µM, and more preferably between 2 and 50 µM, and even more preferably between 5 and 30 µM.

Preferably, the NFL-TBS$_{40-63}$ peptide is added on to the cells during at least 30 minutes, preferably 1 hour, and then the cells are washed extensively in order to remove the free remaining peptide.

Preferably, the NFL-TBS$_{40-63}$ peptide is coupled to a fluorescent dye, directly or through an appropriate carrier, and the presence in the cells is revealed by flow cytometry. More preferably, the fluorescent dyes are contained in lipid nanocapsules that are also coupled to the peptide of the invention.

Alternatively, the NFL-TBS$_{40-63}$ peptide is not labeled and its detection is performed indirectly by conventional means using for example antibodies against all or part of the amino acid sequence. In this case, conventional techniques of indirect detection can be used (e.g. flow cytometry, immunohistochemistry, Western Blot, etc. . . . ).

In a preferred embodiment, the in vitro method of detection of neural stem cells uses the NFL-TBS$_{40-63}$ peptide itself. More preferably, it uses a carboxyfluorescein-labelled NFL-TBS$_{40-63}$ peptide or a biotin-tagged NFL-TBS$_{40-63}$ peptide.

It could furthermore be useful to detect NSCs in vivo in the brain, for example when a tumor is closed to a subventricular zone, or in order to follow the outcome of NSCs during a deleterious/pharmaceutical treatment. Alternatively, it may be useful to detect these cells so as to extract them from the brain of a patient suffering from the Parkinson or Alzheimer disease (by stereotactic aspiration) in order to manipulate them in vitro (e.g., by gene therapy), before re-implantation in the brain of said patient. Finally, it may be useful to recover the NSCs from a patient suffering from multiple sclerosis so as to let oligodendrocytes grow in vitro, before re-implantation in demyelinated zones of said patient brain. Thus, in another embodiment of the invention, the present invention relates to the use of the isolated amino acid sequence comprising the NFL-TBS$_{40\text{-}63}$ peptide, or a biologically active derivative thereof, for detecting the neural stem cells in vivo, or, in other words, the isolated amino acid sequence comprising the NFL-TBS$_{40\text{-}63}$ peptide or a biologically active derivative thereof, for its use for detecting the neural stem cells in vivo.

In this particular embodiment, the amino acid sequence of the invention is preferably labeled with fluorescent dyes or luminescent dyes, directly or through an appropriate carrier (such as nanocapsules), that can be detected in safe conditions during a surgical operation.

For example, the present invention provides a method for in vivo detecting the presence of neural stem cells, said method comprising:

a) labeling an amino acid sequence comprising the NFL-TBS$_{40\text{-}63}$ peptide or a biologically active derivative thereof with a fluorescent or luminescent dye, directly or through an appropriate carrier (such as nanocapsules), b) injecting said amino acid sequence intracerebrally, c) applying a light of particular wave-length (depending on the fluorescent or luminescent dye) onto the brain region where the peptide has been injected, in order to reveal the neural stem cells.

Figure 1:
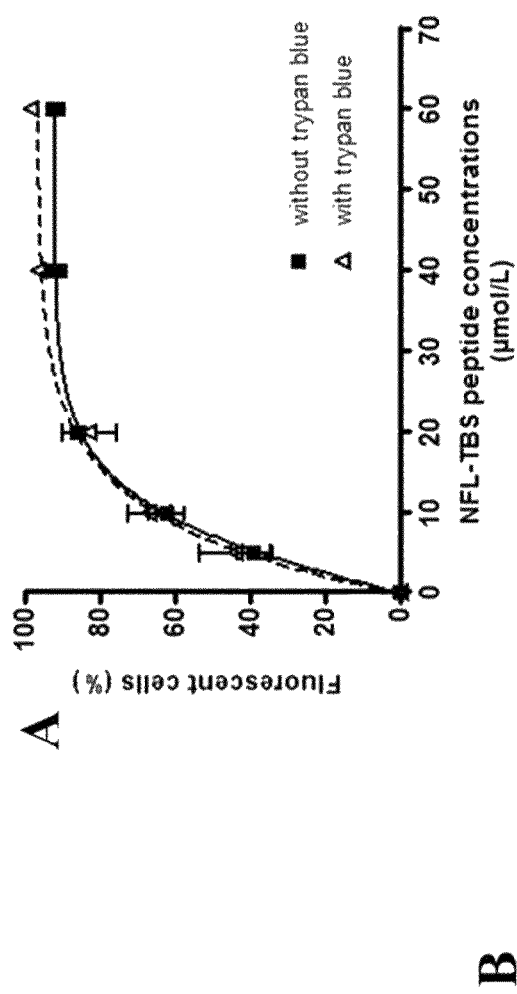
FIG. 1 demonstrates the dose-dependent uptake of the NFL-TBS$_{40\text{-}63}$ peptide in neural stem cells of newborn rats. (A). Neurospheres were incubated with increased concentrations of FITC labelled NFL-TBS$_{40\text{-}63}$ peptide during 30 minutes, and then dissociated before FACS analysis of the peptide uptake in NSC with (dark curve) or without (dotted curve) 0.4% trypan blue. Results represent the percentage of fluorescent cells containing the peptide and compared to cells incubated without the peptide (control). (B) Confocal microscopy of the NFL-TBS$_{40\text{-}63}$ peptide uptake in neural stem cells of newborn rats. Neurospheres were incubated with 20 µmol/L FITC labelled peptide during 6 h, and immunocytochemistry was performed to detect α-tubulin, and the nuclei were stained with DAPI.
Figure 1:
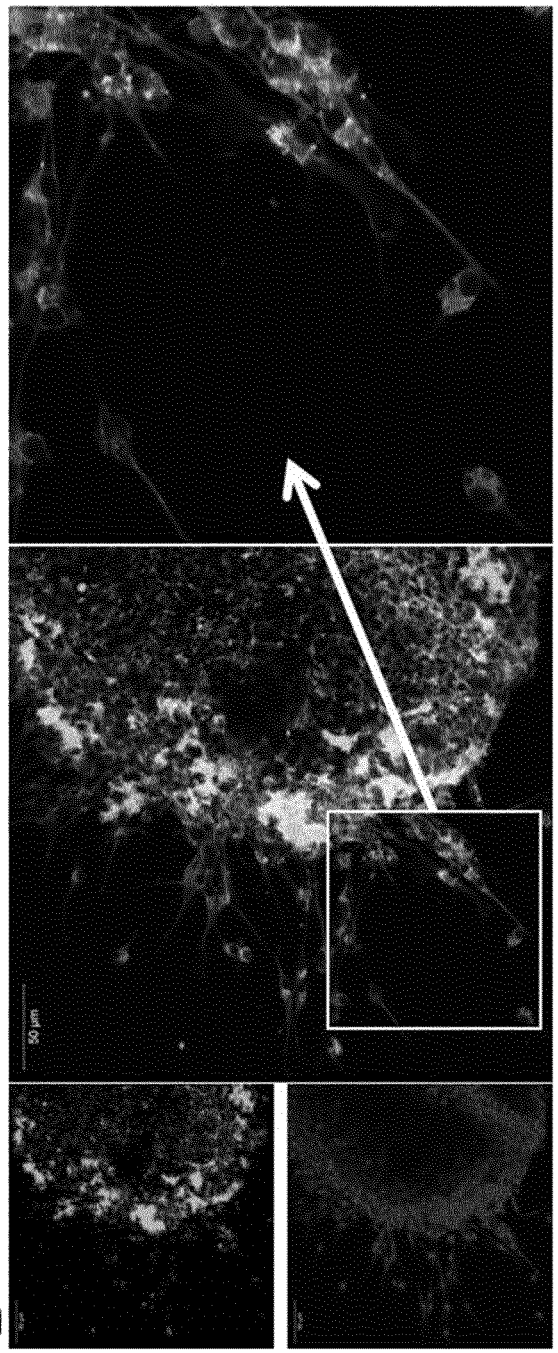

The following examples describe the high specificity and biological effects of the NFL-TBS$_{40-63}$ peptide. They are however not limitative, in particular concerning the nature of amino acid sequence of the invention, and the experimental conditions to use it.

EXAMPLES

Abbreviations: CED: convection-enhanced delivery; DAPI: 4'6-diaminido-2-phenylindole; DAM: 5-(N,N-dimethyl) amiloride hydrochloride; DNA: deoxyribonucleotic acid; DG; dentate gyrus; EGF: epithelial growth factor; FITC: carboxy-fluorescein isothiocyanate; GFAP: glial fibrillary acidic protein; NBCS: new-born calf serum; NFL-TBS: neurofilament light subunit-tubulin binding site; NSC: neural stem cell; PBS: phosphate buffer sodium; PE: R-phycoerythrin; PI: propidium iodide; PMA: phorbol 12-myristate 13-acetate; PSA-NCAM: polysialic acid neural cell adhesion molecule; SEM: standard error of the mean; SVZ: sub-ventricular zone.

Cell Culture and Material

Primary cultures of neural stem cells are derived from the sub-ventricular zone of newborn (1-5 days) or adults (<4 months) brain Wistar rats. The dissociated cells were grown in MEM alpha (PAA) supplemented with 25 mmol/L D-glucose (Sigma), 1 mmol/L Na Pyruvate, 15 mmol/L HEPES, 5% penicillin/streptomycin (PAA) and 1% B27 (Gibco), and containing 20 ng/mL EGF (Promega). After 5-7 days, stem cells formed floating neurospheres.

The peptide was synthesized by Millegen (Toulouse, France) or Eurogentec (Seraing, Belgium). The NFL-TBS$_{40-63}$ peptide (YSSYSAPVSSSLSVRRSYSSSSGS) is biotinylated or coupled to carboxy-fluorescein isothiocyanate (FITC), and dissolved in sterile water.

Chlorpromazine hydrochloride (50 mol/L), phorbol 12-myristate 13-acetate (PMA, 10 g/mL), 5-(N,N-dimethyl) amiloride hydrochloride (DAM, 1 mmol/L), wortmaninn (100 nmol/L), U 0126 (40 µmol/L), sunitinib (1 µmol/L), and colchicine (1 µg/mL) were obtained from Sigma. Genistein (400 µmol/L) was obtained from Merck. Gefitinib (50 µmol/L) was obtained from Santa Cruz Biotechnology.

Flow Cytometry

To evaluate the internalization of the FITC labelled NFL-TBS$_{40-63}$ peptide by the fluorescence-activated cell sorting technique (FACS, Becton Dickinson), neurospheres were seeded in 35-mm dishes and cultured for 30 min at 37° C. in media containing FITC labelled NFL-TBS$_{40-63}$ peptide at increasing concentrations. To quench the extracellular signal of the FITC labelled NFL-TBS$_{40-63}$ peptide, 0.4% trypan blue (Sigma) was added before FACS analysis. To investigate the uptake mechanism, neurospheres were preincubated at 4° C. during 30 min, or with 10 mmol/L sodium azide in the presence of 6 mmol/L 2-deoxy-D-glucose to deplete cellular ATP, or with different inhibitors during 30 min at 37° C. Then 20 µmol/L FITC labelled peptide was added to the cells for 30 min at 37 C.°. Subsequently, after centrifugation (5 min at 700 rpm), cells were dissociated mechanically and washed twice with PBS, and then re-suspended in 50 µg/mL Propidium iodide (PI, Sigma). The fluorescent positive cells that incorporated the FITC labelled peptide were analyzed by flow cytometry (FACSCalibur, Becton Dickinson).

To quantify the PSA-NCAM expression on neural stem cells, neurospheres were seeded in 35-mm dishes and cultured for 7 days at 37° C. in media containing biotinylated NFL-TBS.40-63 peptide at increasing concentrations, or containing 1% new-born calf serum (NBCS). After dissociation, cells were incubated with the anti-PSA-NCAM antibody conjugated to R-phycoerythrin (PE) for 10 minutes at 4° C. (Miltenyi), washed and then re-suspended in 50 µg/mL PI. The fluorescent positive cells that expressed PSA-NCAM were analyzed by flow cytometry.

To investigate the possible effect of the NFL-TBS$_{40-63}$ peptide on the cell cycle, neurospheres were seeded in 35-mm dishes and then treated with increased concentrations of biotinylated NFL-TBS$_{40-63}$ peptide or with 1 µmol/L colchicine during 48 h at 37° C. Neurospheres were then collected in a microcentrifuge tube. After centrifugation (5 min at 700 rpm), cells were dissociated mechanically and permeabilized with PBS-Tween 0.5% and fixed with ethanol 70% before adding 1 mg/mL RNase (Invitrogen) during 30 min at 37° C. The cell suspension was diluted in 10 µg/mL PI before DNA content analysis by flow cytometry.

To analyse the cell viability in the presence of the NFL-TBS$_{40-63}$ peptide, neurospheres were seeded in 35-mm dishes and then treated with increased concentrations of biotinylated peptide or with 1 µmol/L colchicine during 3 or 5 days at 37° C. Neurospheres were then collected in a microcentrifuge tube. After centrifugation (5 min at 700 rpm), cells were dissociated mechanically and stained with annexin-V FITC (Annexin-V FITC Kit, Miltenyi Biotec) for 15 min at room temperature. Finally, cells were counterstained with 1 µg/mL PI solution prior to analysis by flow cytometry.

CyQUANT Cell Proliferation Assay

To analyse the NFL-TBS.40-63 peptide effect on the NSC proliferation, primary neurospheres were dissociated and $5.10^3$ cells per well were plated on BD Cell-Tak (BD Biosciences) on 96 well microplate. Cells were treated with increased concentrations of biotinylated NFL-TBS.40-63 peptide, or with 1 µmol/L colchicine during 72 h at 37° C. After washes with PBS, cells were freezed at −80° C. Finally, the DNA concentration was analyzed using the CyQUANT cell proliferation assay kit (Molecular Probes).

Confocal Microscopy

To visualize the NFL-TBS$_{40-63}$ peptide uptake in neural stem cells, neurospheres were plated on BD Cell-Tak (BD Biosciences) coverslips or LabTek chambers. After 24 h, neurospheres were incubated with 20 µmol/L FITC labelled NFL-TBS$_{40-63}$ peptide for 30 min, 6 h or 72 h. Following PBS washing, cells were fixed with 4% paraformaldehyde for 15 min and washed three times in PBS. They were then incubated in a 0.5% triton X-100 permeabilization solution for 30 min and washed three times in PBS before incubation in a blocking solution (1% bovine serum albumin in 0.1% triton X-100) for 1 h. Neurospheres were then incubated overnight at 4° C. with mouse anti-α-tubulin antibody (Sigma) 1/1000. After three washes in PBS, tubulin was localized using an Alexa 568 nm anti-mouse antibody (Life Technologies) 1/200 for 2 h. Neurospheres were washed three times with PBS before adding 3 µmol/L 4'6-diaminido-2-phenylindole (DAPI, Sigma) for 5 min. Following PBS washing, coverslips were mounted with a ProLong Gold antifade solution (Life Technologies). Stained neurospheres were observed with an inverted fluorescent microscope Leica or with a LSM 700 Zeiss confocal microscope, and images were analysed respectively with Metamorph or Zen 2009 softwares.

Neurosphere Forming and Self-Renewal Analysis

To investigate neurosphere forming properties, $5.10^3$ SVZ cells were seeded per well in a 24 wells plate in media containing 20 ng/mL EGF. Cells were incubated in the absence or presence of increasing concentrations of biotinylated peptide, or with 1 μg/mL colchicine. After 5-7 days, the total number of primary neurospheres and the percent of adherent primary neurospheres were determined in each condition by microscopy analysis, and pictures were taken with an inverted microscope and the Metamorph software. Then for self-renewal assay, primary neurospheres were collected in each condition, dissociated as single cells, and seeded in media containing 20 ng/mL EGF. After 5 days, the total number of secondary neurospheres was counted in each condition by microscopy analysis.

Intra-Ventricular Injection of the NFL-TBS$_{40-63}$ Peptide and Immunohistochemistry All experimental procedures and animal care were achieved in conformity with the guidelines of the French Government and following the approval by the Local Committee for Ethics on Animal Experiments (Comité d'Ethique en Expérimentation Animale des Pays-de-la-Loire).

Adult females Wistar rats were anesthetized by intraperitoneal injection of a mixture of ketamine 10% (80 mg/kg) and xylazine 2% (10 mg/kg). Animals were then placed on a stereotaxic apparatus (David Kopf instruments, Tujunga, Calif.), and a sagital incision was made through the skin to expose the cranium in which a small hole was made using a dental drill, at the appropriate coordinates (−0.8 mm anterior and 1.6 mm lateral to the bregma). A volume of 20 μL of the FITC-peptide 1 mmol/L was injected, using a 10-μL Hamilton syringe (Hamilton glass syringe 70 RN) with a 32-G needle (Hamilton, VWR), at a depth of 4.3 mm from the outer border of the cranium into the right lateral ventricle, and connected through a cannula to a 100-μL Hamilton 22-G syringe (Hamilton glass syringe 810 RN) containing the peptide. A slow-infusion was performed by convection-enhanced delivery (CED) with an osmotic pump (Harvard Apparatus) at a flow rate of 0.5 μL/min. After injection and withdrawal of the needle (0.5 mm/min), the head skin was sutured. Animals were sacrificed 1 hour, 6 hours, or 24 hours after the injection, and brains were removed and frozen, before sectioning them using a Leica cryostat.

For immunohistochemistry, the brain sections (12 μm thick) were fixed with cold methanol during 10 minutes, washed three times in PBS, and blocked with PBS 5% bovine serum albumin at room temperature for 1 hour. The sections were then incubated with mouse anti-GFAP, mouse anti-vimentin (Sigma) and mouse anti-nestin antibodies (R&D) diluted 1/200, 1/200 and 1/500 respectively in PBS 5% bovine serum albumin overnight. After washing three times in PBS, primary antibodies were revealed using an anti-mouse antibody Alexa 568 nm (Life Technologies) 1/200 in PBS 5% bovine serum albumin, and incubated during 90 minutes at room temperature, followed by washing in PBS. The brain sections were then counterstained with 3 μmol/L 4'6-diaminido-2-phenylindole (DAPI, Sigma) for 5 minutes and rinsed twice with PBS. Finally, slides were mounted with a ProLong Gold antifade reagent (Life Technologies), and observed with a Nikon confocal microscope and pictures were taken using the Nikon NIS elements software.

Statistical Analysis

All experiments were repeated at least three times. For FACS analysis, 20.000 events per sample were analysed. Results were presented as mean percentage of fluorescent cells and data were represented as bar graphs with the standard error of the mean (SEM). Statistical analysis was performed with t of Student test by using Prism 3.00 (GraphPad software, San Diego, Calif.). Asterisks indicate significant level versus the control condition: * $P<0.05$;  $P<0.01$; * $P<0.001$.

3. Results

The internalization of the NFL-TBS$_{40-63}$ peptide in neural stem cells of new-born and adult rats was first investigated in vitro and in vivo, and then characterized its uptake mechanism. Then the possible molecular and cellular effects of the peptide on the microtubule network, the cell cycle and viability of NSCs were analysed. Finally, the consequences of the peptide uptake on the fundamental properties of the NSCs, including the neurosphere formation, self-renewal, and differentiation were evaluated.

The NFL-TBS$_{40-63}$ Peptide Penetrates in Neural Stem Cells of New-Born and Adult Rats In Vitro and In Vivo The neural stem cells were incubated with increased concentrations of carboxyfluorescein-tagged peptide for 30 min and then peptide incorporation was evaluated using the sensitive FACS technique. The FIG. 1A showed a dose-dependent uptake of the peptide in the NSC of new-born rats. At 5 μmol/L of FITC-peptide, 38.72±9.08% of newborn NSCs internalized the peptide, and at 40 μmol/L most NSC internalized the peptide (91.07±5.13%). To assess whether the obtained signal in these experiments corresponds to the internalized FITC-peptide, 0.4% trypan blue was added, before the FACS reading, to quench the surface-bound fluorescence of the FITC-peptide. Results showed a dose-dependent uptake of the peptide similar to that without quenching, confirming the intracellular fluorescence of the peptide (FIG. 1A). Moreover, confocal microscopy confirmed the internalization of the peptide in NSCs present in the neurospheres as well as in progenitor cells in the periphery (FIG. 1B).

Figure 2:
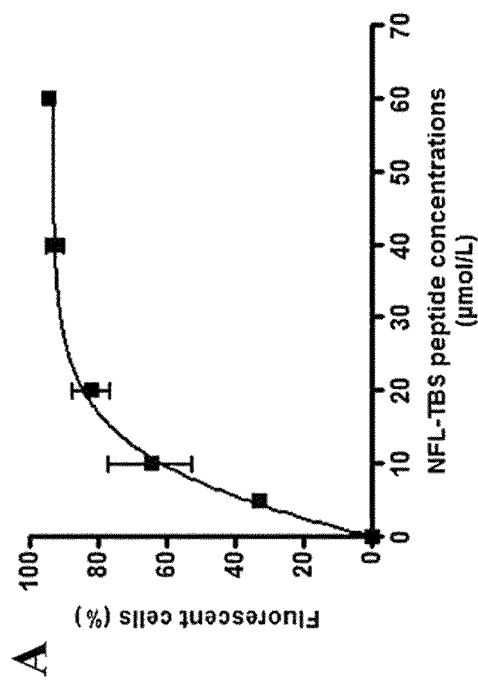
FIG. 2 demonstrates the NFL-TBS$_{40\text{-}63}$ peptide uptake in NSC of adult rats. (A) Dose-dependent uptake of the NFL-TBS$_{40\text{-}63}$ peptide in neural stem cells of adult rats. Neurospheres obtained from adult rats were incubated with increased concentrations of FITC labelled NFL-TBS$_{40\text{-}63}$ peptide during 30 minutes, and then dissociated before FACS analysis. Results represent the percentage of fluorescent cells. (B) Immunohistochemistry of the SVZ of adult rat after in vivo NFL-TBS$_{40\text{-}63}$ peptide injection. Adult rats received 1 mmol/L FITC labelled NFL-TBS$_{40\text{-}63}$ peptide in the right lateral ventricle and they were sacrificed 1 h later. Intermediated filaments expressed in the SVZ were stained with anti-vimentine (1) and anti-GFAP (2) and nucleus with DAPI. The SVZ, delimited with white punctuated lines, was separated from the lateral ventricle by ependymal cells that express vimentine, and within the sub-ependymal zone there are GFAP-expressing cells.
Figure 2:
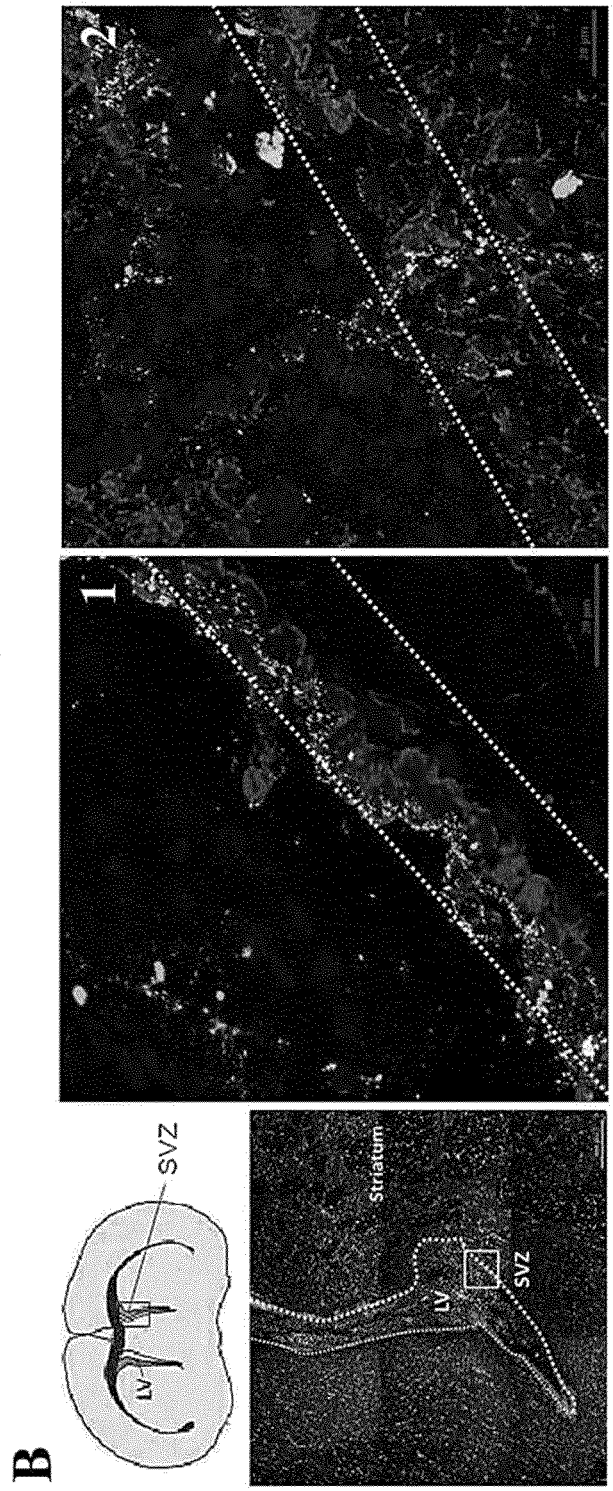

The peptide uptake in adult NSC in vitro was further investigated by flow cytometry and in vivo by injecting the peptide in the lateral ventricle of adult rats followed by immunohistochemistry. The NSC were isolated from adult rat SVZ and incubated with increasing concentrations of FITC-tagged peptide during 30 minutes. The peptide incorporation was evaluated using the sensitive FACS technique. A dose-dependent uptake of the peptide in these cells was observed, with a maximum threshold of 92.74±2.51% reached at 40 μmol/L, similar to the uptake observed by the NSC of newborn rats (FIG. 2A). To test the possible targeted uptake of the peptide in vivo by adult NSC, the FITC-tagged peptide was injected in the right lateral ventricle of adult rats and examined the samples 1 hour after the injection. The SVZ is separated from the lateral ventricles by a layer of ciliated ependymal cells that express vimentin, and there are GFAP-expressing cells in the sub-ependymal zone. The brain section revealed that the peptide is localised in the right lateral ventricle, in the ependymal cells and a part was observed in the SVZ where cells expressed GFAP (FIG. 2B). A similar pattern was observed 6 and 24 hours following the injection of the peptide (data not shown). These confocal analyses indicate that the peptide is internalized in ependymal cells and can cross the ependymal barrier to penetrate in the SVZ where neural stem cells and progenitors were found, without causing detectable cytotoxicity.

Uptake of the NFL-TBS$_{40-63}$ Peptide Through a Passive Transport

Figure 3:
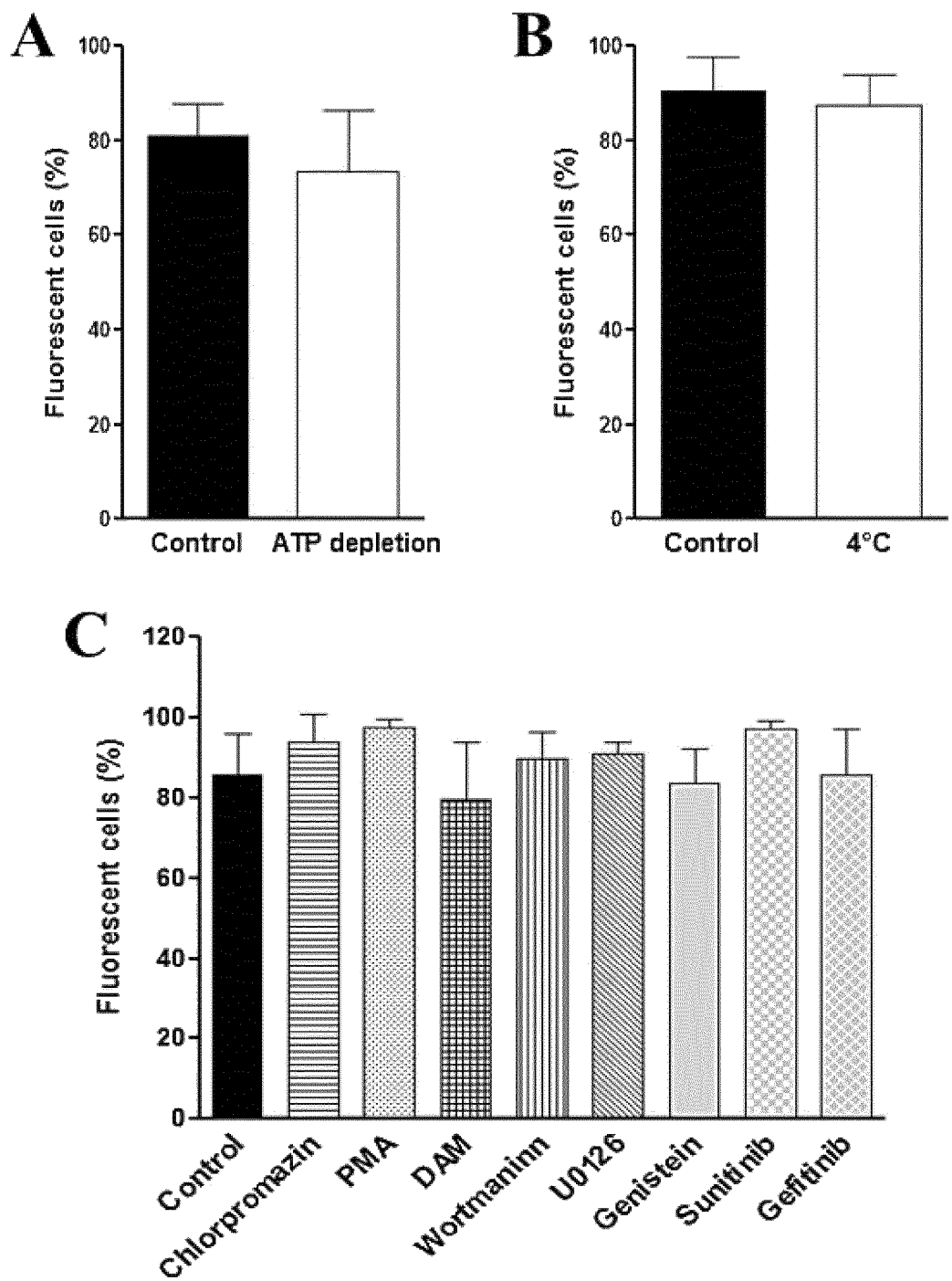
FIG. 3 shows the passive transport of the NFL-TBS$_{40\text{-}63}$ peptide in neural stem cells of newborn rats. Neurospheres were cultured during 30 minutes in normal condition (black column) or in an ATP depleted buffer (A) as well as at 4° C. for 30 min (B). Cells were then incubated in the same conditions with 20 µmol/L FITC labelled NFL-TBS$_{40\text{-}63}$ peptide during 30 min or 1 h respectively. (C) Neurospheres were pre-treated with 50 µmol/L chlorpromazine, 10 µg/mL PMA, 1 mmol/L DAM, 100 nmol/L wortmaninn, 40 µmol/L U0126, 400 µmol/L genistein, 1 µmol/L sunitinib, and 50 µmol/L gefitinib during 30 min. Then they were incubated in the same conditions with 20 µmol/L FITC labelled NFL-TBS$_{40\text{-}63}$ peptide during 30 min. Finally, neurospheres were dissociated to analyse by FACS the peptide uptake. Results represent the percentage of fluorescent cells when compared to the normal (control) condition.

The molecular mechanism involved for the peptide uptake, in particular the endocytosis and the direct translocation, two well-known and major pathways for the internalization of peptides (Stewart et al., 2008) was investigated. The passive or active transports were first evaluated by incubating cells at 4° C. or in an ATP-depleted buffer during 30 minutes prior to add the peptide, and further incubate them during 30 minutes. The peptide uptake was not affected by 4° C. or ATP-depletion, indicating that its internalization in NSCs occurs by a passive mechanism (FIG. 3A et 3B). To further exclude the use of an active transport, a panel of inhibitors for each well-known endocytic pathways was tested, as well as inhibitors of signalling pathways involved in the endocytic mechanism (PI3K, MAPK, growth factor receptors). FIG. 3C shows that in the presence of these inhibitors, the peptide uptake was not affected confirming that it was not internalized in NSCs throught endocytosis.

The NFL-TBS$_{40-63}$ Peptide has No Effect on the Neurosphere Formation but Reduces the Self-Renewal of the Neural Stem Cells by Increasing Cell Attachment Only at High Concentration (100 μmol/L)

Figure 4:
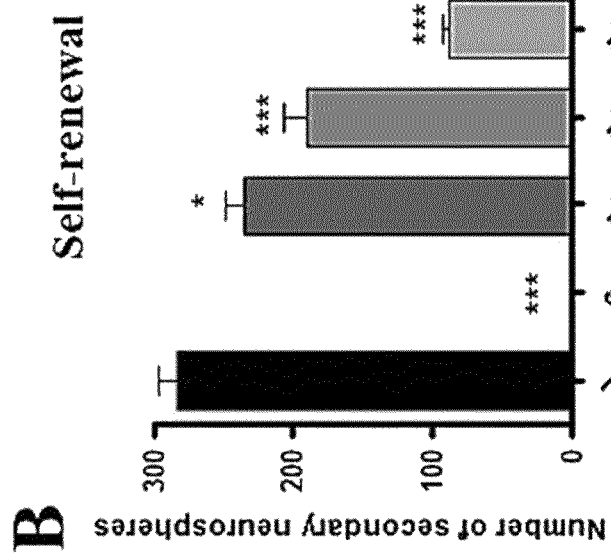
FIG. 4 shows that the NFL-TBS$_{40\text{-}63}$ peptide does not alter the neurospheres formation but disrupts the NSC self-renewal and increases attachment of the cells at high concentrations. (A) To analyse the formation of neurospheres, NSC were incubated with or without increased concentrations of the NFL-TBS$_{40\text{-}63}$ peptide or with 1 µg/mL colchicine during 5-7 days, and the numbers of primary neurospheres were counted in each condition by microscopy analysis. (B) To analyze the NSC self-renewal, the treated primary neurospheres were dissociated, and the numbers of secondary neurospheres were counted after 5 days in each condition by microscopy analysis. The number of treated neurospheres was compared to untreated neurospheres (control). *P<0.05; *P<0.001. (C) The number of adherent primary neurospheres treated with or without the NFL-TBS$_{40\text{-}63}$ peptide was counted by microscopy analysis. The percentage of adherent neurospheres was determined comparatively with the control condition. *P<0.001. (D) Images of the representative morphology of primary neurospheres in each condition were taken with an inverted microscope Leica and the Metamorph software. (E) To quantify the PSA-NCAM expression on NSC, neurospheres were treated with or without increased concentrations of NFL-TBS.40-63 peptide, or with 1% new born calf serum (serum) during 7 days, and the dissociated cells were analysed by FACS after PSA-NCAM labelling. Results represent the percentage of fluorescent cells expressing PSA-NCAM compared to the control condition. (F) To analyze the NSC proliferation, cells were incubated in BD Cell Tak and treated with or without increased concentrations of NFL-TBS.40-63 peptide, or with 1 µg/mL colchicine during 72 h. Then DNA concentration (ng/mL) was quantified using the CyQUANT cell proliferation assay. Results represent the percentage of DNA concentration (ng/mL) compared to the control condition.
Figure 4:
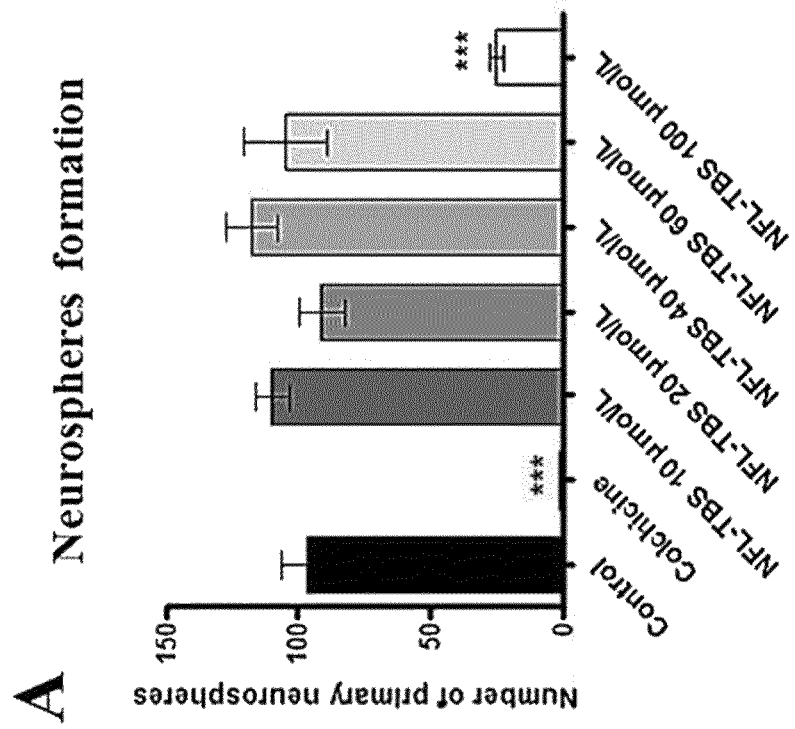
Figure 4:
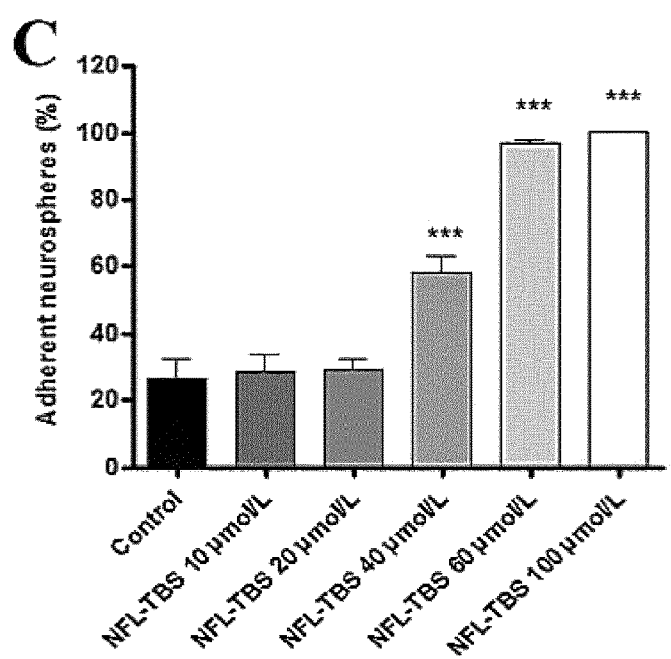
Figure 4:
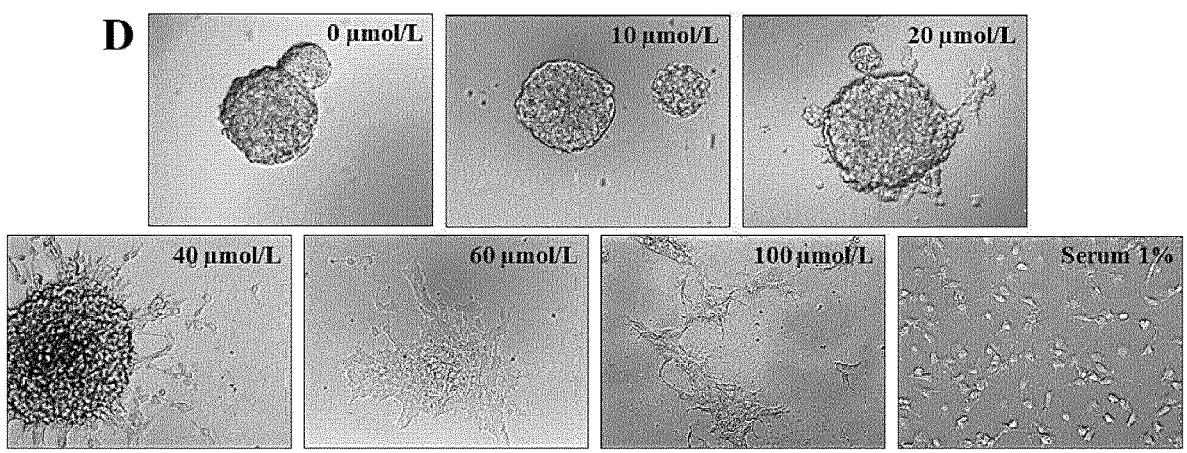
Figure 4:
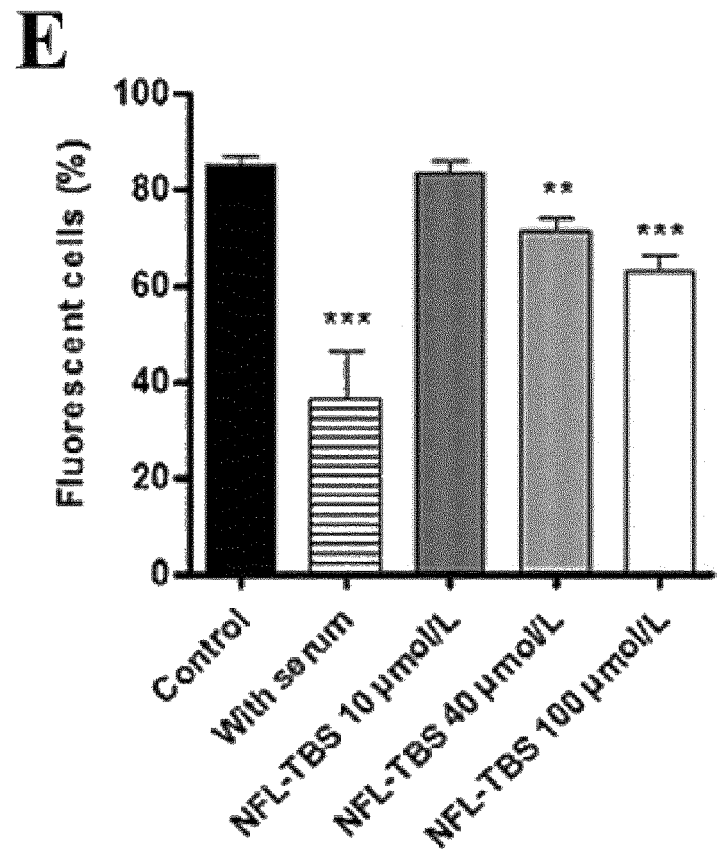
Figure 4:
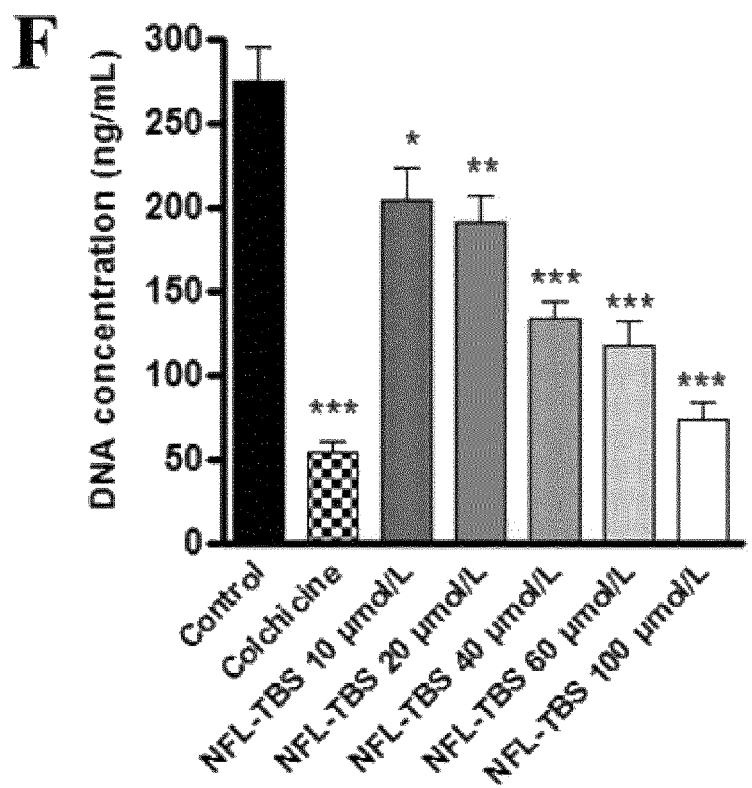

NSCs are characterized in vitro by their capacity to form neurospheres and to self-renew. When NSCs were exposed to increased concentrations of the peptide during 5 days, the number of primary neurospheres did not change when compared to untreated control NSC cultures, except for 100 μmol/L (FIG. 4A). Moreover, results showed that most of primary neurospheres were adherent at 40 μmol/L peptide. At higher peptide concentrations, no floating neurospheres were observed (FIG. 4C). Images of these neurospheres showed increased number of adherent cells that correlated with increased peptide concentrations (FIG. 4D).

This effect was explained by an increased attachment of the neurospheres, and a decreased cell proliferation in the presence of the peptide.

To complete these observations, the PSA-NCAM expression was also analysed. This protein characterizes the neural stem cell growing, by limiting the cell-cell interactions and the cell interactions with the extracellular matrix, and by abolishing cell adhesion (Johnson et al., 2005).

The increased attachment of the neural stem cells at high peptide concentrations is related to a weak decrease of the polysialic acid neural cell adhesion molecule (PSA-NCAM) expression on the neural stem cells. This is also shown when neural stem cells were incubated with 1% NBCS (FIG. 4E).

Moreover, results showed a significant decrease of the neural stem cell proliferation when cells are incubated one week with increased peptide concentrations, as shown with colchicine, an anti-proliferative agent. These results indicated that the peptide alters the proliferation of the neural stem cells from low peptide concentrations, and that this effect is more important at higher concentrations (FIG. 4F).

Thus, in this study, high concentrations of the peptide decrease the PSA-NCAM expression in neural stem cells, and therefore explain their increased adhesion.

To investigate the self-renewal capacity of NSC, the primary neurospheres cultured with or without peptide were dissociated and replaced for 5 days in culture medium only. The dissociated cells, from primary neurospheres previously cultured with peptide, generated significantly lower numbers of secondary neurospheres, when compared to control NSC cultures (FIG. 4B). In these experiments a positive control was used by exposing NSC to 1 μg/mL colchicine that blocks cell proliferation. Together, these results showed that the peptide has no effect on the neurosphere formation (except at high concentration 100 μmol/L), but it affects the self-renewal of neural stem cells with an increased cell attachment and a decreased cell proliferation.

Figure 5:
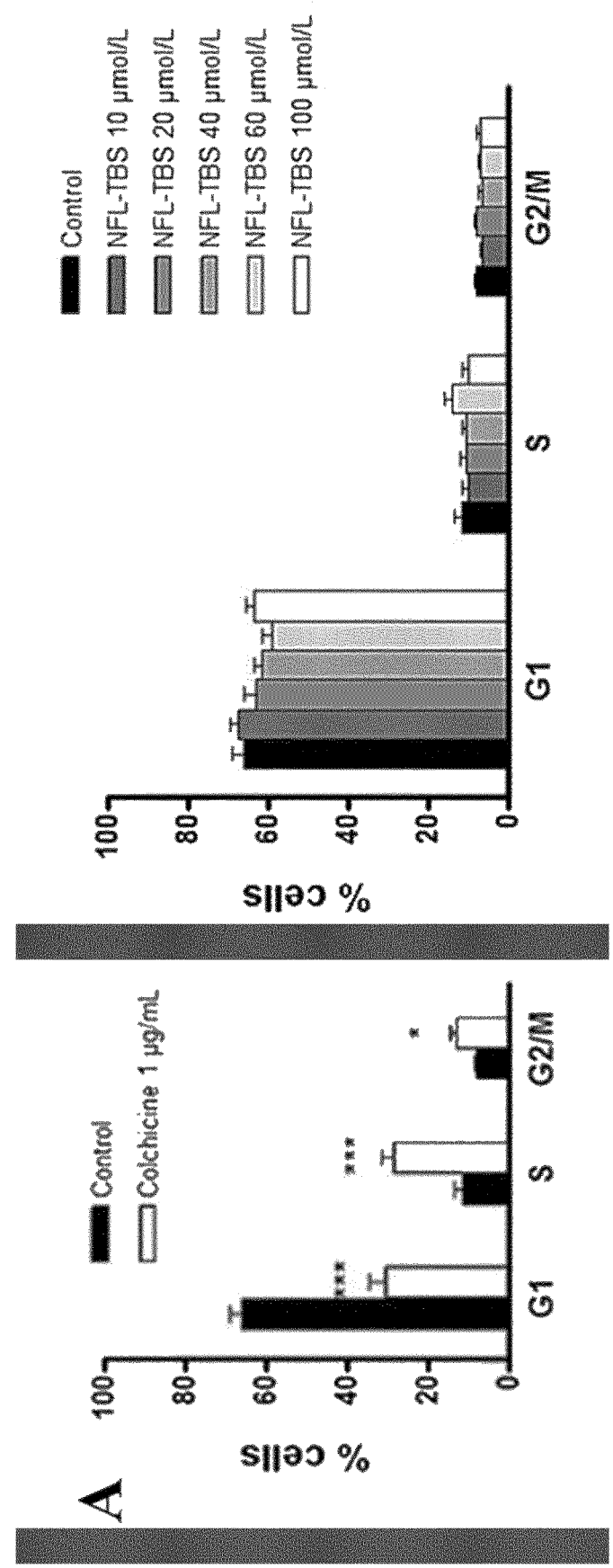
FIG. 5 shows that the NFL-TBS$_{40\text{-}63}$ peptide has no effect on the cell cycle and the viability of neural stem cells. (A) Neurospheres were treated during 48 hours with increased concentrations of the NFL-TBS$_{40\text{-}63}$ peptide, or with 1 µg/mL colchicine. Then neurospheres were dissociated and cell cycle analysis was performed by PI incorporation and FACS reading. The percentage of cells in each phase of the cell cycle was determined comparatively with untreated cells (control). *P<0.05; *P<0.001. (B) NSC were cultured on coated LabTek chambers and incubated with 20 µmol/L FITC labelled peptide. Immunocytochemistry was then performed to reveal the microtubule network with an anti-α-tubulin. Images were analysed with the Metamorph software. (C) Neurospheres were treated with increased concentrations of the NFL-TBS$_{40\text{-}63}$ peptide, or with 1 µg/mL colchicine, for 72 h. Then neurospheres were dissociated and cell viability analysis was performed by Annexin V/PI staining and FACS reading. The percentage of viable cells was determined comparatively with cells incubated in the same conditions but without peptide (control). *P<0.001.
Figure 5:
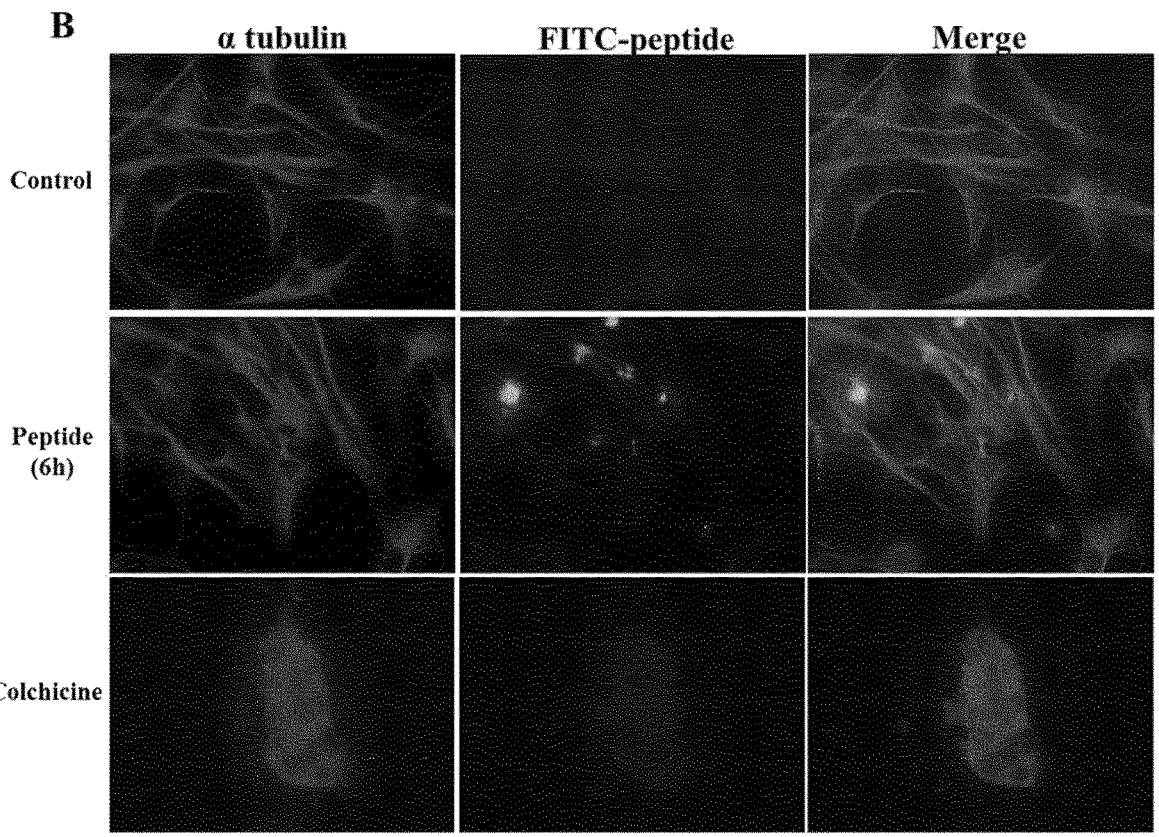
Figure 5:
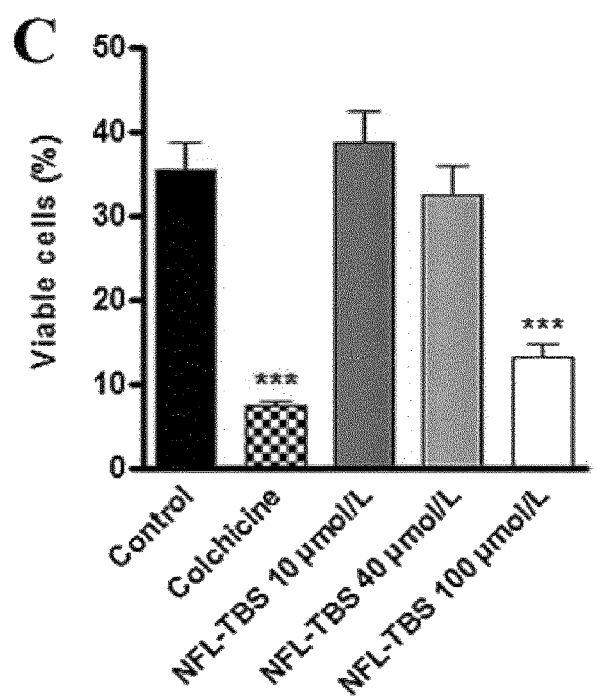

The NFL-TBS$_{40-63}$ Peptide has No Detectable Cytotoxic Effect on Neural Stem Cells It has been shown that the peptide disrupts the microtubule formation in glioblastoma cells at concentrations higher than 10 μm, and consequently disrupts the cellular cycle. However, such effects were not observed in normal cells like neurones and astrocytes (Bocquet et al., 2009; Bergès et al., 2012). To investigate the peptide effect in NSC, the cellular cycle of NSC was analysed in the presence of increased concentrations of the peptide during 48 h, by using FACS analysis. With or without peptide, the cellular cycle of NSC remained unchanged with approximately 60-65% of cells in G1-phase, 10% in S-phase and 7% in G2/M-phases. The cellular cycle of NSC was only affected in the presence of 1 μg/mL colchicine, used as a positive control to disrupt the microtubule network (FIG. 5A). These results show that to the opposite of glioblastoma cells, the peptide has no effect on the cellular division of NSC (Bergès et al., 2012). Moreover, confocal microscopy showed that following 6 hours of incubation with the peptide, the microtubule network of NSC was not affected, whereas colchicine profoundly affected the microtubule network (FIG. 5B). It was also showed that the peptide has no major effect in the NSC viability. Cells were treated three days with increased concentrations of the peptide or with colchicine, stained with Annexin V-FITC and PI, and then analysed by flow cytometry. The number of viable cells was strongly reduced when treated with colchicine, but the cell viability was not modified in the presence of the peptide (FIG. 5C).

Figure 6:
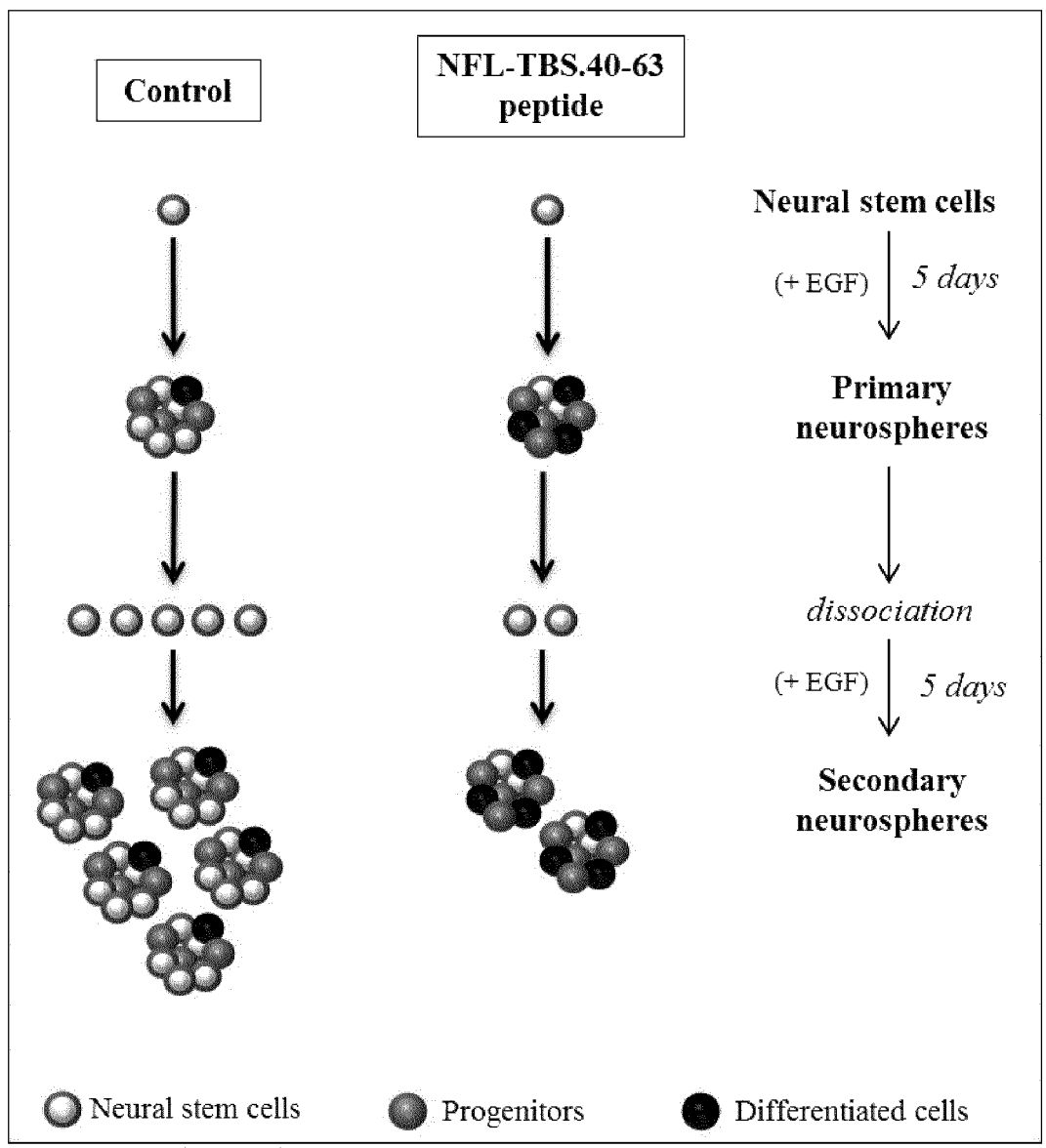
FIG. 6 shows the hypothetic effect of the NFL-TBS$_{40\text{-}63}$ peptide on the neural stem cells. In the presence of the peptide and EGF the neurosphere formation was not affected whereas the self-renewal capacity was reduced, with increased stem cell attachment and probably increased differentiated cells.

To summarize, these results indicate that at low concentrations (up to 20 μmol/L), the peptide disrupts cell proliferation without effect on cell attachment, whereas at high concentrations (from 40 μmol/L), the peptide affects both proliferation and adhesion of neural stem cells, characterizing a possible differentiation of neural stem cells into progenitors or differentiated cells (FIG. 6).

BIBLIOGRAPHIC REFERENCES

Agasse et al., 2004. Neurogenic and intact or apoptotic non-neurogenic areas of adult brain release diffusible molecules that differentially modulate the development of subventricular zone cell cultures. Eur J Neurosci. 2004 March; 19(6):1459-68.

Ahmed et al., 2009. Transcription factors and neural stem cell self-renewal, growth and differentiation. Cell Adh Migr. 3(4):412-24.

Azari H, Rahman M, Sharififar S, Reynolds B A (2010) Isolation and expansion of the adult mouse neural stem cells using the neurosphere assay. J Vis Exp (45)

Balzeau J, Pinier M, Berges R, Saulnier P, Benoit J P, Eyer J (2013) The effect of functionalizing lipid nanocapsules with NFL-TBS.40-63 peptide on their uptake by glioblastoma cells. Biomaterials 34 (13):3381-3389

Beckervordersandforth R, Tripathi P, Ninkovic J, Bayam E, Lepier A, Stempfhuber B, Kirchhoff F, Hirrlinger J, Haslinger A, Lie D C, Beckers J, Yoder B, Irmler M, Gotz M (2010) In vivo fate mapping and expression analysis reveals molecular hallmarks of prospectively isolated adult neural stem cells. Cell Stem Cell 7 (6):744-758

Berges R, Balzeau J, Peterson A C, Eyer J (2012) A tubulin binding peptide targets glioma cells disrupting their microtubules, blocking migration, and inducing apoptosis. Mol Ther 20 (7):1367-1377

Bexell D, Svensson A, Bengzon J (2013) Stem cell-based therapy for malignant glioma. Cancer Treat Rev 39 (4): 358-365

Bocquet A, Berges R, Frank R, Robert P, Peterson A C, Eyer J (2009) Neurofilaments bind tubulin and modulate its polymerization. J Neurosci 29 (35):11043-11054

Coskun V, Wu H, Blanchi B, Tsao S, Kim K, Zhao J, Biancotti J C, Hutnick L, Krueger R C, Jr., Fan G, de Vellis J, Sun Y E (2008) CD133+ neural stem cells in the ependyma of mammalian postnatal forebrain. *Proc Natl Acad Sci USA* 105 (3):1026-1031

Gage FH (2000) Mammalian neural stem cells. *Science* 287 (5457):1433-1438

Hall P A, Watt F M (1989) Stem cells: the generation and maintenance of cellular diversity. *Development* 106 (4): 619-633

Jo J, Song H, Park S G, Lee S H, Ko J J, Park J H, Jeong J, Cheon Y P, Lee D R (2012) Regulation of differentiation potential of human mesenchymal stem cells by intracytoplasmic delivery of coactivator-associated arginine methyltransferase 1 protein using cell-penetrating peptide. *Stem Cells* 30 (8):1703-1713

Johnson C P, Fujimoto I, Rutishauser U, Leckband D E (2005) Direct evidence that neural cell adhesion molecule (NCAM) polysialylation increases intermembrane repulsion and abrogates adhesion. *J Biol Chem* 280 (1):137-145

Katsetos C D, Draberova E, Legido A, Dumontet C, Draber P (2009) Tubulin targets in the pathobiology and therapy of glioblastoma multiforme. I. Class III beta-tubulin. *J Cell Physiol* 221 (3):505-513

Kim S U, Lee H J, Kim Y B (2013) Neural stem cell-based treatment for neurodegenerative diseases. *Neuropathology* 33 (5):491-504

Lei Y, Tang H, Yao L, Yu R, Feng M, Zou B (2008) Applications of mesenchymal stem cells labeled with Tat peptide conjugated quantum dots to cell tracking in mouse body. *Bioconjug Chem* 19 (2):421-427

Lendahl U, Zimmerman L B, McKay R D (1990) CNS stem cells express a new class of intermediate filament protein. *Cell* 60 (4):585-595

Lepinoux-Chambaud C, Eyer J (2013) The NFL-TBS.40-63 anti-glioblastoma peptide enters selectively in glioma cells by endocytosis. *Int J Pharm* 454 (2):738-747

Nakamura Y, Yamamoto M, Oda E, Yamamoto A, Kanemura Y, Hara M, Suzuki A, Yamasaki M, Okano H (2003) Expression of tubulin beta II in neural stem/progenitor cells and radial fibers during human fetal brain development. *Lab Invest* 83 (4):479-489

Oh M. C. and Lim D. A., 2009. Novel treatment strategies for malignant gliomas using neural stem cells. *Neurotherapeutics.* 6(3):458-64. doi: 10.1016/j.nurt.2009.05.003.

Reigner B, Blesch K. Estimating the starting dose for entry into humans: principles and practice. European *Journal of Clinical Pharmacology.* 2002; 57(12):835-845.

Reynolds B A, Weiss S (1992) Generation of neurons and astrocytes from isolated cells of the adult mammalian central nervous system. *Science* 255 (5052):1707-1710

Shah B S, Clark P A, Moioli E K, Stroscio M A, Mao J J (2007) Labeling of mesenchymal stem cells by bioconjugated quantum dots. *Nano Lett* 7 (10):3071-3079

Stewart K M, Horton K L, Kelley S O (2008) Cell-penetrating peptides as delivery vehicles for biology and medicine. *Org Biomol Chem* 6 (13):2242-2255

Suh H, Consiglio A, Ray J, Sawai T, D'Amour K A, Gage F H (2007) In vivo fate analysis reveals the multipotent and self-renewal capacities of Sox2+ neural stem cells in the adult hippocampus. *Cell Stem Cell* 1 (5):515-528

Taupin P., 2011. Neurogenic drugs and compounds to treat CNS diseases and disorders. *Cent Nerv Syst Agents Med Chem.* 1; 11(1):35-7.

Weigmann A, Corbeil D, Hellwig A, Huttner W B (1997) Prominin, a novel microvilli-specific polytopic membrane protein of the apical surface of epithelial cells, is targeted to plasmalemmal protrusions of non-epithelial cells. *Proc Natl Acad Sci USA* 94 (23): 12425-12430

Yukawa H, Noguchi H, Nakase I, Miyamoto Y, Oishi K, Hamajima N, Futaki S, Hayashi S (2010) Transduction of cell-penetrating peptides into induced pluripotent stem cells. *Cell Transplant* 19 (6):901-909

The invention claimed is:

1. A method of treating neural stem cells comprising
administering directly into the lateral ventricles of a subject an effective amount of a composition comprising an isolated amino acid sequence comprising:
an NFL-TBS$_{40-63}$ peptide (SEQ ID NO: 1), or
a biologically active fragment comprising at least 18 successive amino-acids of SEQ ID NO:1, or
a biologically active variant thereof having at least 95% of identity with SEQ ID NO:1, or
any combination thereof,
wherein the composition targets neural stem cells in vivo, and
wherein the subject is suffering from a neurodegenerative disease.

2. The method of claim 1, wherein said biologically active variant or said biologically active fragment retains a biological activity and a specificity of the NFL-TBS$_{40\text{-}63}$ peptide (SEQ ID NO: 1).

3. The method of claim 1, wherein the composition induces neural stem cell differentiation or reduces neural stem cell self-renewal in vivo.

4. The method of claim 1, wherein said composition comprises chemical compounds or biological materials coupled to the amino acid comprising said peptide, said biologically active fragment or said biologically active variant.

5. The method of claim 4, wherein said chemical compounds or biological materials are contained in nanocapsules, liposomes, or in micelles.

6. The method of claim 4, wherein said chemical compounds or biological materials treat neurodegenerative disorders or neurodegenerative diseases.

7. A method of treating neural stem cells comprising administering directly into the lateral ventricles of a subject an effective amount of an isolated amino acid sequence comprising:
   an NFL-TBS$_{40\text{-}63}$ peptide (SEQ ID NO: 1), or
   a biologically active fragment comprising at least 18 successive amino-acids of SEQ ID NO:1, or
   a biologically active variant thereof having at least 95% of identity with SEQ ID NO:1, or
   any combination thereof,
   wherein the isolated amino acid sequence targets neural stem cells in vivo, and
   wherein the subject is suffering from neurodegenerative diseases.

8. The method of claim 7, wherein said biologically active variant or said biologically active fragment retains a biological activity and a specificity of the NFL-TBS$_{40\text{-}63}$ peptide (SEQ ID NO: 1).

9. The method of claim 7, wherein the isolated amino acid sequence comprising the NFL-TBS$_{40\text{-}63}$ peptide (SEQ ID NO: 1), or said biologically active fragment or variant thereof, induces neural stem cell differentiation or reduces neural stem cell self-renewal in vivo.

10. The method of claim 7, wherein said amino acid sequence comprises chemical compounds or biological materials coupled thereto or to said derivatives.

11. The method of claim 10, wherein said chemical compounds or biological materials are contained in nanocapsules, liposomes, or in micelles.

12. The method of claim 10, wherein said chemical compounds or biological materials treat neurodegenerative disorders or neurodegenerative diseases.

13. The method of claim 10, wherein said chemical compounds or biological materials are directly coupled to the NFL-TBS$_{40\text{-}63}$ peptide, or to said derivative.

* * * * *

SEQUENCE LISTING

```
<160> NUMBER OF SEQ ID NOS: 1

<210> SEQ ID NO 1
<211> LENGTH: 24
<212> TYPE: PRT
<213> ORGANISM: artificial
<220> FEATURE:
<223> OTHER INFORMATION: TBS motif of the human light chain
      neurofilament protein, amino acids

<400> SEQUENCE: 1

Tyr Ser Ser Tyr Ser Ala Pro Val Ser Ser Ser Leu Ser Val Arg Arg
1               5                   10                  15

Ser Tyr Ser Ser Ser Ser Gly Ser
            20
```